(12) United States Patent
Nørremark

(10) Patent No.: US 8,785,494 B2
(45) Date of Patent: Jul. 22, 2014

(54) CALCIUM SENSING RECEPTOR MODULATING COMPOUNDS AND PHARMACEUTICAL USE THEREOF

(75) Inventor: Bjarne Nørremark, Stenløse (DK)

(73) Assignee: LEO-Pharma A/S, Ballerup (DK)

( * ) Notice: Subject to any disclaimer, the term of this patent is extended or adjusted under 35 U.S.C. 154(b) by 367 days.

(21) Appl. No.: 13/322,522

(22) PCT Filed: May 26, 2010

(86) PCT No.: PCT/DK2010/000068
§ 371 (c)(1),
(2), (4) Date: Feb. 2, 2012

(87) PCT Pub. No.: WO2010/136035
PCT Pub. Date: Dec. 2, 2010

(65) Prior Publication Data
US 2012/0129926 A1      May 24, 2012

Related U.S. Application Data

(60) Provisional application No. 61/181,571, filed on May 27, 2009, provisional application No. 61/262,425, filed on Nov. 18, 2009.

(30) Foreign Application Priority Data

May 27, 2009  (DK) ................................ 2009 00665

(51) Int. Cl.
| | | |
|---|---|---|
| A61K 31/21 | (2006.01) | |
| A61K 31/215 | (2006.01) | |
| A61K 31/195 | (2006.01) | |
| A61K 31/135 | (2006.01) | |

(52) U.S. Cl.
CPC .................................. A61K 31/195 (2013.01)
USPC ........... 514/510; 514/530; 514/567; 514/647; 560/45; 560/47; 560/51; 560/53; 560/104; 562/452; 562/456

(58) Field of Classification Search
USPC ........ 514/510, 530, 567, 647; 560/45, 47, 51, 560/53, 104; 562/452, 456
See application file for complete search history.

(56) References Cited

U.S. PATENT DOCUMENTS

| | | |
|---|---|---|
| 6,362,231 B1 | 3/2002 | Sakai et al. |
| 2003/0199497 A1 | 10/2003 | Ruat et al. |
| 2005/0032796 A1 | 2/2005 | Shinagawa et al. |
| 2005/0192317 A1 | 9/2005 | Dauban et al. |
| 2006/0069098 A1 | 3/2006 | Miyoshi et al. |
| 2006/0135572 A1 | 6/2006 | Shinagawa et al. |
| 2011/0218160 A1 | 9/2011 | Miyazaki et al. |

FOREIGN PATENT DOCUMENTS

| | | |
|---|---|---|
| EP | 1203761 A2 | 5/2002 |
| EP | 1281702 A2 | 2/2003 |
| EP | 1757582 A1 | 2/2007 |
| EP | 2 341 044 A1 | 7/2011 |
| WO | WO 93/04373 A1 | 3/1993 |
| WO | WO 95/11221 A1 | 4/1995 |
| WO | WO 96/12697 A2 | 5/1996 |
| WO | WO 97/41090 A1 | 11/1997 |
| WO | WO 98/01417 A1 | 1/1998 |
| WO | WO 00/21910 A2 | 4/2000 |
| WO | WO 01/34562 A1 | 5/2001 |
| WO | WO 01/90069 A1 | 11/2001 |
| WO | WO 02/12181 A1 | 2/2002 |
| WO | WO 02/059102 A3 | 8/2002 |
| WO | WO 03/099776 A1 | 12/2003 |
| WO | WO 03/099814 A1 | 12/2003 |
| WO | WO 2004/056365 A2 | 7/2004 |
| WO | WO 2004/069793 A2 | 8/2004 |
| WO | WO 2004/094362 A1 | 11/2004 |
| WO | WO 2004/106280 A1 | 12/2004 |
| WO | WO 2004/106295 A2 | 12/2004 |
| WO | WO 2004/106296 A2 | 12/2004 |
| WO | WO 2005/034928 A1 | 4/2005 |
| WO | WO 2005/065050 A2 | 7/2005 |
| WO | WO 2005/068433 A1 | 7/2005 |
| WO | WO 2005/115975 A1 | 12/2005 |
| WO | WO 2006/001958 A2 | 1/2006 |
| WO | WO 2006/047195 A2 | 5/2006 |
| WO | WO 2009/025792 A2 | 2/2009 |
| WO | WO 2009/051718 A2 | 4/2009 |
| WO | WO 2009/065406 A2 | 5/2009 |
| WO | WO 2010/021351 A1 | 2/2010 |

OTHER PUBLICATIONS

International Search Report, dated Dec. 1, 2010, issued in PCT/DK2010/000068.
Balfour et al., "Cinacalcet Hydrochloride", Drugs, vol. 65, No. 2, 2005, pp. 271-281.
Brown, "Ca2+-Sensing Receptor", American Society for Bone and Mineral Research, 2008, pp. 134-141.
Chattopadhyay et al., "The Calcium-Sensing Receptor: A Window into the Physiology and Pathophysiology of Mineral Ion Metabolism", Endocrine Reviews, vol. 17, No. 4, 1996, pp. 289-307.
Dong, "Cinacalcet: An Oral Calcimimetic Agent for the Management of Hyperparathyroidism", Clinical Therapeutics, vol. 27, No. 11, 2005, pp. 1725-1751.

(Continued)

*Primary Examiner* — Raymond Henley, III
(74) *Attorney, Agent, or Firm* — Birch, Stewart, Kolasch & Birch, LLP

(57) ABSTRACT

The invention relates to novel calcium-sensing receptor (CaSR) modulating trifluoromethylphenylene cyclopentylene compounds represented in formula (I) and derivatives thereof, to said compounds for use as a medicament, to said compounds for use in therapy, to pharmaceutical compositions comprising said compounds, to methods of treating diseases with said compounds, and to the use of said compounds in the manufacture of medicaments.

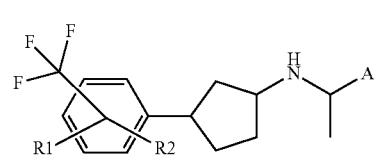

(I)

16 Claims, No Drawings

(56) References Cited

OTHER PUBLICATIONS

Drueke, "Modulation and action of the calcium-sensing receptor", Nephrol Dial Transplant, vol. 19, Suppl. 5, 2004, pp. v20-v26.

Feng et al., "Easily Accessible C2-Symmetric Chiral Bicyclo[3.3.0] Dienes as Ligands for Rhodium-Catalyzed Asymmetric 1,4-Addition", Chemistry an Asian Journal, vol. 3, 2008, pp. 1511-1516.

Harrington et al., "Calcium Sensing Receptor Activators: Calcimimetics", Current Medicinal Chemistry, vol. 14, 2007, pp. 3027-3034.

Hashimoto et al., "Enantioselective Intramolecular C-H Insertion Reactions of α-Diazo β-Keto Esters Catalyzed by Dirhodium(II) Tetrakis[N-phthaloyl-(S)-phenylalaninate]: The Effect of the Substituent at the Insertion Site on Enantioselectivity", Synlett, May 1994, pp. 353-355.

International Search Report dated Dec. 14, 2010, for Application No. PCT/DK2010/000069.

International Search Report dated Sep. 21, 2010, for Application No. PCT/DK2010/000070.

Osigweh et al., "Regulation of colonic crypt fluid and electrolyte secretion by the calcium sensing receptor", Alimentary Tract II, vol. 201, No. 3S, Sep. 2005, p. S17.

Varchi et al., "Copper Catalyzed Conjugate Addition of Highly Functionalized Arylmagnesium Compounds to Enones", Tetrahedron, vol. 56, 2000, pp. 2727-2731.

Wallace et al., "Scalable Synthesis and Isolation of the Four Stereoisomers of Methyl 1-Amino-3-(4-bromophenyl)cyclopentanecarboxylate, Useful Intermediates for the Synthesis of S1P1 Receptor Agonists", J. Org. Chem., vol. 74, 2009, pp. 4886-4889.

Whitfield, "The Bone-Building Action of the Parathyroid Hormone; Implications for the Treatment of Osteoporosis", Drugs & Aging, vol. 15, No. 2, Aug. 1999, pp. 117-129.

Ye et al., "Amyloid-β Protiens Activate Ca2+-Permeable Channels Through Calcium-Sensing Receptors", Journal of Neuroscience Research, vol. 47, 1997, pp. 547-554.

Yu et al., "Rhodium-Catalyzed Asymmetric 1,4-Addition of Heteroaryl Cyclic Triolborate to α,β-Unsaturated Carbonyl Compounds", Synett, No. 6, 2009, pp. 0994-0998.

Yu, et al., "Supporting Information of : Rhodium-Catalyzed Asymmetric 1,4-Addition of Heteroaryl Cyclic Triolborate to α,β-Unsaturated Carbonyl Compounds", Synett, DOI: 10.1055/s-0028-1088198, 2008, pp. 1-15.

CALCIUM SENSING RECEPTOR MODULATING COMPOUNDS AND PHARMACEUTICAL USE THEREOF

This application is the National Phase of PCT/DK2010/000068 filed on May 26, 2010, which claims priority under 35 U.S.C. 119(e) to U.S. Provisional Application No(s). 61/181,571 filed on May 27, 2009 and 61/262,425 filed on Nov. 18, 2009 and under U.S.C. 119(a) to Patent Application No. PA 2009 00665 filed in Denmark on May 27, 2009, all of which are hereby expressly incorporated by reference into the present application.

FIELD OF THE INVENTION

This invention relates to novel calcium-sensing receptor (CaSR) modulating trifluoromethylphenylene cyclopentylene compounds and derivatives thereof, to said compounds for use as a medicament, to said compounds for use in therapy, to pharmaceutical compositions comprising said compounds, to methods of treating diseases with said compounds, and to the use of said compounds in the manufacture of medicaments.

BACKGROUND OF THE INVENTION

The calcium-sensing receptor (CaSR) is a G-protein-coupled receptor (GPCR) that signals through the activation of phospholipase C, increasing levels of inositol 1,4,5-triphosphate and cytosolic calcium. The CaSR belongs to the subfamily C of the GPCR superfamily, which also includes receptors for glutamate, gamma aminobutyric acid (GABA), pheromones and odorants that all possess a very large extra-cellular domain. This domain is highly negatively charged and is involved in binding of calcium and other positively charged molecules. The CaSR is found in the parathyroid glands but has also been identified in the brain, intestine, pituitary, thyroid glands, bone tissue and kidneys [Brown, E. M. Calcium-Sensing Receptor. *Primer of the Metabolic Bone Diseases and Disorders of Mineral Metabolism* Fifth Edition, 2003 by American Society for Bone and Mineral Research, Chapter 17, p. 111; Drueke, T. E. *Nephrol Dial Transplant* (2004) 19, suppl 5, v20-v26].

The calcium-sensing receptor (CaSR) detects changes in extra-cellular calcium concentration and initiates the functional response of this cell, which is a modulation of the secretion of the parathyroid hormone (PTH). Secretion of PTH increases extra-cellular calcium ion concentration by acting on various cells, such as bone and kidney cells, and the extra-cellular calcium ion concentration reciprocally inhibits the secretion of PTH by acting on parathyroid cells. The reciprocal relationship between calcium concentration and PTH level is an essential mechanism for calcium homeostasis maintenance.

The calcimimetic activity corresponds to the ability to produce or induce biological responses observed through variations in the concentration of extracellular calcium ions $(Ca^{2+})_e$ and extracellular magnesium ions $(Mg^{2+})_e$. $(Ca^{2+})_e$ and $(Mg^{2+})_e$ ions play a major role in the body since they regulate calcium homeostasis on which the vital functions of the body depend. Thus, hypo- and hypercalcemia, that is to say conditions in which $(Ca^{2+})_e$ ions are below or above the mean threshold, have a major effect on many functions, such as cardiac, renal or intestinal functions. They deeply affect the central nervous system (Chattopadhyay et al. Endocr. Review, 1996).

It has been shown that $Ca^{2+}$ and $Mg^{2+}$ ions, but also $Ba^{2+}$ ions, within millimolar concentration ranges, stimulate CaSRs. Activation of CaSRs might be induced in the brain by β-amyloid peptides, which are involved in neurodegenerative diseases such as Alzheimer's disease [Ye et al, 3. Neurosci. Res., 47, 547-554, 1997].

Disturbance of CaSR activity is associated with biological disorders such as primary and secondary hyperparathyroidism, osteoporosis, cardiovascular, gastrointestinal, endocrine and neurodegenerative diseases, or certain cancers in which $(Ca^{2+})_e$ ions are abnormally high.

Primary hyperparathyroidism (primary HPT) is characterised by elevated levels of PTH and serum calcium which is typically caused by adenoma or hyperplasia of the parathyroid gland. It can result in bone pain and excessive bone resorption.

Secondary hyperparathyroidism (secondary HPT) often develops in patients who have reduced kidney function and is characterised by elevated levels of PTH. The underlying causes are complex, but a reduced ability to convert vitamin D to calcitriol and elevated levels of phosphorus play significant roles in the development of secondary HPT. If left untreated, the clinical manifestations of secondary HPT include bone and joint pain and limb deformities [Harrington, P. E. and Fotsch, C. Calcium Sensing Receptor Activators: Calcimimetics. Current Medicinal Chemistry, 2007, 14, 3027-3034].

A reduced kidney function or renal failure is also accompanied by renal osteodystrophy, e.g. osteitis fibrosa, osteomalacia, adynamic bone disease, or osteoporosis. The disorders are characterized by either high or low bone turnover. Osteoporosis is a multifactor disease which depends in particular on age and sex. While menopausal women are very greatly affected, osteoporosis is increasingly proving to be a problem in elderly men, and, for the moment, no really satisfactory treatments exist. Its social cost may become even heavier in the years to come, particularly as life expectancy is becoming longer. Osteoporosis is currently treated with estrogens, calcitonin or biphosphonates which prevent bone resorption without stimulating bone growth. More recent data demonstrate that intermittent increases in PTH or in derivatives thereof are effective in the treatment of osteoporosis and make it possible to remodel bone by stimulating bone formation [Whitfield et al., Drugs & Aging 1999 August; 15 (2): 117-129 1999]. This new therapeutic approach for treatment of osteoporosis appears to be very advantageous, although major problems are associated with the use of PTH hormone, such as the route of injection, but also the appearance of tumours, observed recently during clinical trials in humans. Intermittent secretion of endogenous PTH can be obtained by blocking the calcium sensing receptor. The blocking of PTH secretion with CaSR agonists may be followed by a rapid increase in PTH (rebound effect), which is then beneficial in the treatment of osteoporosis.

A compound having an activating effect on CaSR (CaSR agonist), that is, a compound which selectively acts on CaSR to mimic or strengthen the action of $Ca^{2+}$, is called a calcimimetic. On the other hand, a compound having an antagonistic effect on CaSR (CaSR antagonist, that is, a compound which suppresses or inhibits the action of $Ca^{2+}$), is called a calcilytic.

The calcium-sensing receptor has recently been found to be a potent target for developing therapeutic options such as using calcimimetics for treatment of diarrhea. [Osigweh et al, J American Coll. of Surgeons, V201, Issue 3, suppl 1, September 2005, p 17.]

Calcimimetics have been shown to be commercially useful for the treatment of hyperparathyroidism (HPT): The calcimimetic compound Cinacalcet® [Balfour, J. A. B. et al. *Drugs* (2005) 65(2), 271-281; Lindberg et. al. *J. Am. Soc. Nephrol* (2005), 16, 800-807, Clinical Therapeutics (2005), 27(11), 1725-1751] is commercially available for the treatment of secondary HPT in chronic kidney disease patients on dialysis and for the treatment of primary HPT in patients with parathyroid carcinoma. Thus, proof of concept for activators of calcium sensing receptor (CaSR) in humans has been achieved and the clinical relevance is well established.

Other calcimimetic compounds were for example described in WO02/059102, WO98/001417, WO05/065050, WO03/099814, WO03/099776, WO00/21910, WO01/34562, WO01/090069, WO97/41090, U.S. Pat. No. 6,001,884, WO96/12697, EP1203761, WO95/11221, WO93/04373, EP1281702, WO02/12181, WO04/56365, WO04/069793, WO04/094362, US2004242602, WO04/106280, WO04/106295, WO04/106296, WO05/068433, WO05/115975, EP1757582, WO2009/051718 and WO2010/021351.

SUMMARY OF THE INVENTION

It has surprisingly been found that the novel compounds of the present invention are modulators, e.g. activators or agonists of the human calcium sensing receptor (CaSR) and may thus be useful in the treatment or prophylaxis of a number of diseases or physiological disorders involving modulation of CaSR activity.

The present invention provides novel trifluoromethylphenylene cyclopentylene compounds wherein the phenylene ring is further substituted, having advantageous pharmacokinetic properties.

Accordingly the present invention relates to a compound according to formula I

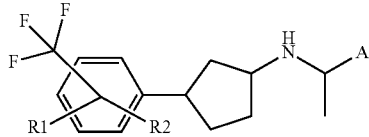

wherein
A represents $C_{6-10}$aryl, $C_{1-9}$heterocycloalkylphenyl, $C_{1-9}$heteroaryl or $C_{3-7}$cycloalkyl, wherein said $C_{6-10}$aryl, $C_{1-9}$heterocycloalkylphenyl, $C_{1-9}$heteroaryl or $C_{3-7}$cycloalkyl is optionally further substituted with one or more, same or different substituents represented by halogen, hydroxy, mercapto, trifluoromethyl, cyano, carboxy, —C(O)H, —NH$_2$, —C(O)NH$_2$, nitro, oxo, —S(O)$_2$NH$_2$, $C_{1-6}$alkyl, $C_{2-6}$alkenyl, $C_{2-6}$alkynyl, $C_{1-6}$hydroxyalkyl, $C_{1-6}$haloalkyl, $C_{1-6}$alkoxy, $C_{1-4}$alkoxycarbonyl, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-7}$cycloalkyl, $C_{3-7}$cycloalkenyl, $C_{1-6}$-amino, iminomethyl, $C_{1-6}$aminosulfonyl, $C_{1-4}$-aminocarbonyloxy, $C_{1-4}$alkylsulfonylamino, hydroxyiminomethyl, $C_{1-4}$alkylcarbonylamino, $C_{1-6}$heterocycloalkyl, $C_{2-6}$heterocycloalkenyl, $C_{1-5}$heteroaryl or phenyl;
$R_1$ represents one or more, same or different substituents selected from halogen, cyano, —NH$_2$, carboxy, $C_{1-6}$-amino, hydroxy, mercapto, —C(O)H, —C(O)NH$_2$, nitro, oxo, hydroxymethyl, $C_{1-6}$alkoxy, carboxy$C_{1-4}$alkoxy, $C_{1-6}$alkoxycarbonyl, $C_{1-6}$alkoxycarbonyl$C_{1-6}$alkoxy, carboxy$C_{1-4}$alkyl, $C_{1-6}$alkoxycarbonyl$C_{1-4}$alkyl, $C_{1-6}$alkylcarbonyl, $C_{1-6}$aminocarbonyl, hydroxyaminocarbonyl, $C_{3-6}$cycloalkylaminocarbonyl, $C_{1-6}$heterocycloalkylaminocarbonyl, $C_{3-6}$cycloalkylamino, $C_{1-6}$heterocycloalkylcarbonyl, $C_{6-14}$aryl, $C_{1-9}$heteroaryl, $C_{1-6}$heteroarylaminocarbonyl, —S(O)$_2$NH$_2$, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-6}$heterocycloalkyloxy, $C_{1-6}$-aminosulfonyl, $C_{1-6}$-aminocarbonyloxy, $C_{1-6}$alkylsulfonylamino, $C_{1-6}$alkylsulfonylamino$C_{1-3}$alkyl, $C_{6-10}$arylamino, $C_{6-10}$arylaminocarbonyl, $C_{6-10}$aryloxycarbonyl, $C_{1-6}$alkoxycarbamoyl, $C_{6-10}$arylcarbonylamino, $C_{6-10}$arylsulfonylamino, $C_{1-6}$alkylcarbonylamino, $C_{1-3}$alkylcarbonylamino$C_{1-3}$alkyl, $C_{2-6}$alkenylcarbonylamino, $C_{3-6}$cycloalkenylcarbonylamino, $C_{3-6}$cycloalkylcarbonylamino, $C_{1-4}$alkoxycarbonylamino, $C_{1-6}$heterocycloalkylcarbonylamino, $C_{1-6}$alkylsulfonyl, $C_{1-6}$heterocycloalkylsulfonyl or $C_{1-4}$alkylsulfonylaminocarbonyl, iminomethyl, hydroxyiminomethyl, amidino, trifluoromethyl, $C_{1-6}$alkyl, $C_{2-4}$alkenyl, $C_{2-6}$alkynyl, $C_{1-6}$hydroxyalkyl, amino$C_{1-6}$alkyl, $C_{1-6}$haloalkyl, $C_{3-7}$cycloalkyl, $C_{3-7}$cycloalkenyl, $C_{1-6}$heterocycloalkyl, $C_{2-6}$heterocycloalkenyl, methoxycarbonyl$C_{1-3}$alkyl or carboxy$C_{6-10}$aryl, wherein said $C_{1-6}$-amino, $C_{1-6}$alkoxy, carboxy$C_{1-4}$alkoxy, $C_{1-6}$alkoxycarbonyl, $C_{1-6}$ alkylcarbonyl, $C_{1-6}$-aminocarbonyl, $C_{3-6}$cycloalkylaminocarbonyl, $C_{1-6}$heterocycloalkylaminocarbonyl, $C_{3-6}$cycloalkylamino, $C_{1-6}$heterocycloalkylcarbonyl, $C_{6-14}$ aryl, $C_{1-9}$heteroaryl, $C_{1-6}$heteroarylaminocarbonyl, $C_{1-6}$ureido, $C_{1-6}$thioureido, $C_{1-4}$ alkylcarbonyloxy, $C_{1-4}$alkoxycarbonyloxy, $C_{1-4}$alkoxysulfonyloxy, $C_{1-6}$heterocycloalkyloxy, $C_{1-6}$alkylthio, $C_{1-6}$-aminosulfonyl, $C_{1-6}$-aminocarbonyloxy, $C_{1-6}$alkylsulfonylamino, $C_{1-6}$alkylsulfonylamino$C_{1-3}$ alkyl, $C_{6-10}$arylamino, $C_{6-10}$arylaminocarbonyl, $C_{6-10}$ aryloxycarbonyl, $C_{1-4}$alkoxycarbamoyl, $C_{6-10}$arylcarbonylamino, $C_{6-10}$arylsulfonylamino, $C_{1-6}$alkylcarbonylamino, $C_{2-6}$alkenylcarbonylamino, $C_{3-6}$cycloalkenylcarbonylamino, $C_{3-6}$cycloalkylcarbonylamino, $C_{1-6}$alkoxycarbonylamino, $C_{1-6}$heterocycloalkylcarbonylamino, $C_{1-6}$alkylsulfonyl, $C_{1-6}$heterocycloalkylsulfonyl or $C_{1-4}$alkylsulfonylaminocarbonyl, $C_{1-6}$alkyl, $C_{2-6}$alkenyl, $C_{2-6}$alkynyl, $C_{1-6}$hydroxyalkyl, amino$C_{1-6}$alkyl, $C_{1-6}$haloalkyl, $C_{3-7}$cycloalkyl, $C_{3-7}$cycloalkenyl, $C_{1-6}$heterocycloalkyl, $C_{2-6}$heterocycloalkenyl, or carboxy$C_{6-10}$ aryl are optionally substituted with one or more, same or different substituents selected from the group consisting of halogen, trifluoromethyl, hydroxy, cyano or $C_{1-4}$alkyl;
$R_2$ represents one or more, same or different substituents selected from hydrogen, cyano, halogen, carboxy, —C(O)NH$_2$, $C_{1-4}$alkyl, $C_{2-4}$alkenyl, $C_{2-4}$alkynyl, $C_{1-6}$hydroxyalkyl, $C_{1-6}$haloalkyl, amino$C_{1-6}$alkyl, $C_{3-6}$cycloalkyl, $C_{1-6}$heterocycloalkyl, $C_{1-6}$alkoxy, $C_{1-6}$aminocarbonyl, $C_{6-10}$aryloxycarbonyl, $C_{1-6}$amino, $C_{6-10}$arylamino, $C_{1-4}$alkoxycarbonylamino, $C_{1-4}$alkylcarbonylamino, $C_{2-4}$alkenylcarbonylamino, $C_{3-6}$cycloalkylcarbonylamino or $C_{1-6}$heterocycloalkylcarbonylamino,
or pharmaceutically acceptable stereoisomers, salts or in vivo hydrolysable esters thereof.

In another aspect, the present invention relates the use of a compound of general formula I as defined herein as a medicament in therapy.

In yet another aspect, the invention relates to the use of a compound of general formula I as defined herein in the treatment, amelioration or prophylaxis of physiological disorders or diseases associated with disturbances of CaSR activity, such as hyperparathyroidism.

In a still further aspect, the invention relates to the use of a compound of general formula I as defined herein for the manufacture of a medicament for the treatment, amelioration or prophylaxis of physiological disorders or diseases associated with disturbances of CaSR activity, such as hyperparathyroidism.

In a still further aspect, the invention relates to a pharmaceutical composition comprising a compound of general formula I as defined herein or a pharmaceutically acceptable stereoisomer, salt, or in vivo hydrolysable ester thereof together with a pharmaceutically acceptable vehicle or excipient.

In a still further aspect, the invention relates to a method of preventing, treating or ameliorating parathyroid carcinoma, parathyroid adenoma, primary parathyroid hyperplasia, cardiac, renal or intestinal dysfunctions, diseases of the central nervous system, chronic renal failure, chronic kidney disease, polycystic kidney disorder, podocyte-related diseases, primary hyperparathyroidism, secondary hyperparathyroidism, tertiary hyperparathyroidism, anaemia, cardiovascular diseases, osteitis fibrosa, adynamic bone disease, osteoporosis, steroid induced osteoporosis, senile osteoporosis, post menopausal osteoporosis, osteomalacia and related bone disorders, bone loss post renal transplantation, gastrointestinal diseases, endocrine and neurodegenerative diseases, cancer, Alzheimer's disease, IBS, IBD, malassimilation, malnutrition, abnormal intestinal motility such as diarrhea, vascular calcification, abnormal calcium homeostasis, hypercalcemia, or renal bone diseases, the method comprising administering to a patient in need thereof an effective amount of a compound of general formula I as defined herein, optionally in combination or as supplement with an active vitamin-D sterol or vitamin-D derivative, such as 1-α-hydroxycholecalciferol, ergocalciferol, cholecalciferol, 25-hydroxycholecalciferol, 1-α-25-dihydroxycholecalciferol, or in combination or as supplement with phosphate binders, estrogens, calcitonin or biphosphonates.

DETAILED DESCRIPTION OF THE INVENTION

Definitions

The term "formula I" when referred to in the description, includes both formula I, Ia and Ib.

The term "cycloalkyl" is intended to indicate a saturated cycloalkane radical, comprising 3-7 carbon atoms, such as 4-7 or 3-6 carbon atoms, such as 4-6 or 5-6 carbon atoms, e.g. cyclopentyl or cyclohexyl.

The term "cycloalkenyl" is intended to indicate a mono-, or di-unsaturated non-aromatic cyclic hydrocarbon radical, comprising 3-7 carbon atoms, such as 4-7, such as 3-6 carbon atoms, such as 4-6 or preferably 5-6 carbon atoms, e.g. cyclobutenyl, cyclopentenyl, or cyclohexenyl.

The term "heterocycloalkyl" is intended to include a cycloalkyl radical as defined above, comprising 1-6 carbon atoms, in particular a 4-, 5- or 6-membered ring, comprising 1-5 carbon atoms and 1-5 hetero atoms (selected from O, S and N), such as 2-5 carbon atoms and 1-4 hetero atoms, or 3-5 carbon atoms and 1-3 hetero atoms selected from O, S, or N, e.g. piperidyl, piperidino, morpholino, morpholinyl, pyrrolidinyl, tetrahydro-furyl, or tetrahydropyranyl.

The term "heterocycloalkenyl" is intended to indicate a cycloalkenyl radical as defined above, comprising 2-6 carbon atoms, such as 2-6 carbon atoms, in particular a 5- or 6-membered ring, comprising 2-5 carbon atoms and 1-5 hetero atoms (selected from O, S and N), such as 3-5 carbon atoms and 1-3 hetero atoms, preferably 4-5 carbon atoms and 1-2 hetero atoms selected from O, S, or N.

The term "heterocycloalkylphenyl" is intended to include radicals of heterocycloalkyl ring, in particular a 5- or 6-membered ring, comprising 1-5 carbon atoms and 1-4 heteroatoms, selected from O, N or S, such as 2-5 carbon atoms and 1-3 heteroatoms, preferably 3-5 carbon atoms and 1-2 heteroatoms, the heterocycloalkyl ring being fused or annelated with phenyl, e.g. 2,3-dihydro-benzofuranyl, 1,3-benzodioxolyl or 2,3-dihydro-benzo[1,4]dioxinyl.

The term "aryl" is intended to indicate a radical of (an) aromatic carbocyclic ring(s) comprising 6-14 carbon atoms, preferably 6-10 carbon atoms, in particular 6-membered rings, optionally fused or annelated carbocyclic rings with at least one aromatic ring, e.g. phenyl, naphthyl, 1-naphthyl or indanyl.

The term "heteroaryl" is intended to include radicals of (a) heterocyclic aromatic ring(s), comprising 1-4 heteroatoms (selected from O, S and N) and 1-9 carbon atoms, such as 1-4 heteroatoms and 2-9 carbon atoms, such as 1-3 heteroatoms and 3-9 carbon atoms, such as 1-2 heteroatoms and 3-5 carbon atoms, or such as 1-2 heteroatoms and 7-9 carbon atoms, preferably 5- or 6-membered rings with 1-3 heteroatoms and 3-9 carbon atoms, or 1-2 heteroatoms and 7-9 carbon atoms, or 1-2 heteroatoms and 3-5 carbon atoms selected from O, S and N, e.g. quinolinyl, indolyl, thienyl, thiazolyl or tetrazolyl.

The term "halogen" is intended to indicate a substituent from the $7^{th}$ main group of the periodic table, preferably fluoro, chloro, iodo or bromo.

In the present context, the term "alkyl" is intended to indicate the radical obtained when one hydrogen atom is removed from a hydrocarbon. Said alkyl comprises 1-6, preferably 1-4 or 1-3, such as 2-4 or 1-2 carbon atoms. The term includes the subclasses normal alkyl (n-alkyl), secondary and tertiary alkyl, e.g. methyl, ethyl, n-propyl, isopropyl, n-butyl, isobutyl, sec-butyl, tert-butyl, pentyl, isopentyl, hexyl or isohexyl.

The term "alkenyl" is intended to indicate a mono-, di-, or triunsaturated hydrocarbon radical comprising 2-6 carbon atoms, in particular 2-4 carbon atoms, such as 2-3 carbon atoms, e.g. vinyl, allyl, propenyl, butenyl, pentenyl or hexenyl.

The term "alkynyl" is intended to indicate a hydrocarbon radical comprising 1-3 C—C triple bonds, e.g. 1, 2 or 3 triple bonds and 2-6 carbon atoms, the alkynyl chain typically comprising 2-5 carbon atoms, in particular 2-4 carbon atoms, such as 2-3 carbon atoms, e.g. ethynyl, propynyl, butynyl or pentynyl.

The term "hydroxyalkyl" is intended to indicate an alkyl radical as defined above, wherein one, two, three or more hydrogen atoms are replaced by hydroxy, e.g. hydroxymethyl, hydroxyethyl, hydroxypropyl, hydroxybutyl etc.

The term "haloalkyl" is intended to indicate an alkyl radical as defined above, wherein one, two, three or more hydrogen atoms are replaced by halogen, same or different, such as iodo, chloro, bromo and/or fluoro, e.g. fluoroethyl, difluoroethyl, difluoromethyl or trifluoromethyl.

The term "alkoxy" is intended to indicate a radical of the formula —OR, wherein R is alkyl or alkenyl as indicated above, e.g. methoxy, ethoxy, n-propoxy, isopropoxy, butoxy, tert-butoxy.

The term "carboxyalkoxy" is intended to indicate a radical of the formula —OR—C(O)OH, wherein R is alkyl or alkenyl as indicated above, e.g. carboxymethoxy, carboxylsopropoxy.

The term "alkylcarbonyl" is intended to indicate a radical of the formula —C(O)—R, wherein R represents alkyl as indicated above, e.g. methylcarbonyl, ethylcarbonyl.

The term "alkoxycarbonylalkoxy" is intended to indicate a radical of the formula —OR—C(O)—OR, wherein R is alkyl as indicated above, e.g. methoxycarbonylmethoxy, methoxycarbonylethoxy, ethoxycarbonylmethoxy, or ethoxycarbonylethoxy.

The term "alkoxycarbonyl" is intended to indicate a radical of the formula —C(O)—O—R, wherein R is alkyl as indicated above, e.g. methoxycarbonyl, ethoxycarbonyl, n-propoxycarbonyl, isopropoxycarbonyl, or tert-butoxycarbonyl.

The term "alkoxycarbonylalkyl" is intended to indicate a radical of the formula —R—C(O)—O—R', wherein R is alkyl as indicated above, e.g. methoxycarbonylmethyl, methoxycarbonylethyl, methoxycarbonylpropyl, ethoxycarbonylethyl.

The term "carboxyalkyl" is intended to indicate a radical of the formula —R—C(O)OH, wherein R is alkyl or alkenyl as indicated above, e.g. carboxymethyl, carboxyethyl, carboxyIsopropyl, carboxypropyl.

The term "alkylcarbonyloxy" is intended to indicate a radical of the formula —O—C(O)—R, wherein R is alkyl as indicated above, e.g. methylcarbonyloxy, or ethylcarbonyloxy.

The term "alkoxycarbonyloxo" is intended to indicate a radical of the formula —O—C(O)—O—R, wherein R is alkyl as indicated above, e.g. methoxycarbonyloxo or ethoxycarbonyloxo.

The term "alkoxycarbamoyl" is intended to indicate a radical of the formula —C(O)NR'—O—R, wherein R' is hydrogen or alkyl as indicated above, and R is alkyl as indicated above, e.g. methoxycarbamoyl.

The term "amino" is intended to indicate a radical of the formula —NRR', wherein R and R' independently represent hydrogen, alkyl or alkenyl, as indicated above, e.g. methylamino, ethylamino, propylamino, dimethylamino, diethylamino or isopropylamino.

The term "aminoalkyl" in intended to indicate an alkyl radical as defined above wherein one or two hydrogen atoms are replaced by —NH$_2$, e.g. aminomethyl, aminoethyl or aminopropyl.

The term "aminocarbonyloxy" is intended to indicate a radical of the formula —O—C(O)—NRR', wherein R and R' independently represent hydrogen or alkyl as indicated above.

The term "amidino" is intended to indicate the radical —C(=NH)NH$_2$.

The term "iminomethyl" is intended to indicate the radical —CH=NH. The term "hydroxyiminomethyl" is intended to indicate the radical —CH=N—(OH).

The term "cycloalkylamino" is intended to indicate a radical of the formula —NRR', wherein R represents hydrogen or alkyl and R' represents cycloalkyl as indicated above.

The term "arylamino" is intended to indicate a radical of the formula —NRR', wherein R represents hydrogen or alkyl as indicated above and R' represents aryl as indicated above.

The term "carboxyaryl" is intended to indicate a radical of the formula —Ar—C(O)OH, wherein Ar represents aryl as indicated above, e.g. carboxyphenyl.

The term "heterocycloalkylcarbonyl" is intended to indicate a radical of the formula —C(O)—R, wherein R is heterocycloalkyl as indicated below.

The term "aminocarbonyl" is intended to indicate a radical of the formula —C(O)—NR'$_2$, wherein each R' is independently hydrogen, alkyl as indicated above, e.g. methylaminocarbonyl or ethylaminocarbonyl.

The term "hydroxyaminocarbonyl" is intended to indicate a radical of the formula —C(O)—NR'—OH, wherein R' is independently hydrogen or alkyl as indicated above.

The term "arylaminocarbonyl" is intended to indicate a radical of the formula —C(O)—NR'-aryl, wherein R' is independently hydrogen or alkyl as indicated above and aryl is as indicated above.

The term "heteroarylaminocarbonyl" is intended to indicate a radical of the formula —C(O)—NR'-heteroaryl, wherein R' is independently hydrogen or alkyl as indicated above and heteroaryl is as indicated above.

The term "cycloalkylaminocarbonyl" is intended to indicate a radical of the formula —C(O)—NR'-cycloalkyl, wherein R' is independently hydrogen or alkyl as indicated above and cycloalkyl is as indicated above.

The term "heterocycloalkylaminocarbonyl" is intended to indicate a radical of the formula —C(O)—NR'-heterocycloalkyl, wherein R' is independently hydrogen or alkyl as indicated above and heterocycloalkyl is as indicated above, e.g. piperidylaminocarbonyl.

The term "heterocycloalkyloxy" is intended to indicate a radical of the formula —O—R, wherein R is a heterocycloalkyl as indicated above.

The term "aminosulfonyl" is intended to indicate a radical of the formula —S(O)$_2$—NR$_2$, wherein each R independently represents hydrogen or alkyl as indicated above, e.g. methylaminosulfonyl or ethylaminosulfonyl.

The term "alkylsulfonylaminocarbonyl" is intended to indicate a radical of the formula —C(O)—NR'—S(O)$_2$—R, wherein R' is independently hydrogen, alkyl or cycloalkyl as indicated above and R is alkyl as indicated above.

The term "aryloxycarbonyl" is intended to indicate a radical of the formula —C(O)—O—R wherein R is aryl as indicated above.

The term "alkylthio" is intended to indicate a radical of the formula —S—R, wherein R is alkyl as indicated above.

The term "alkylsulfonyl" is intended to indicate a radical of the formula —S(O)$_2$—R, wherein R is alkyl as indicated above, e.g. methylsulfonyl.

The term "arylsulfonyl" is intended to indicate a radical of the formula —S(O)$_2$—R, wherein R is aryl as indicated above, e.g. phenylsulfonyl.

The term "heterocycloalkylsulfonyl" is intended to indicate a radical of the formula —S(O)$_2$—R, wherein R is a heterocycloalkyl as indicated above, e.g. morpholinesulfonyl.

The term "alkylcarbonylamino" is intended to indicate a radical of the formula —NR'—C(O)—R, wherein R' is hydrogen or alkyl as indicated above, and R is alkyl as indicated above, e.g. methylcarbonylamino.

The term "alkylcarbonylaminoalkyl" is intended to indicate a radical of the formula —R—NR'—C(O)—R, wherein R' is hydrogen or alkyl as indicated above, and R is alkyl as indicated above, e.g. methylcarbonylaminomethyl.

The term "alkoxycarbonylamino" is intended to indicate a radical of the formula —NR'—C(O)—O—R, wherein R' is hydrogen or alkyl as indicated above, and R is alkyl as indicated above.

The term "alkylsulfonylamino" is intended to indicate a radical of the formula —NR'—S(O)$_2$—R, wherein R is alkyl as indicated above, and R' is hydrogen or alkyl as indicated above, e.g. methylsulfonylamino, ethylsulfonylamino, propylsulfonylamino or butylsulfonylamino.

The term "alkylsulfonylaminoalkyl" is intended to indicate a radical of the formula —R—NR'—S(O)$_2$—R, wherein R is alkyl as indicated above, and R' is hydrogen or alkyl as indicated above, e.g. methylsulfonylaminomethyl.

The term "arylsulfonylamino" is intended to indicate a radical of the formula —NR'—S(O)₂—R, wherein R is aryl as indicated above, and R' is hydrogen, or alkyl as indicated above.

The term "alkoxysulfonyloxy" is intended to represent a radical of the formula —O—S(O)₂—O—R, wherein R is alkyl as indicated above.

The term "arylcarbonylamino" is intended to indicate a radical of the formula —NR'—C(O)—R, wherein R' is hydrogen or alkyl as indicated above, and R is aryl as indicated above.

The term "alkenylcarbonylamino" is intended to indicate a radical of the formula —NR'—C(O)—R, wherein R' is hydrogen or alkyl as indicated above, and R is alkenyl as indicated above.

The term "cycloalkylcarbonylamino" is intended to indicate a radical of the formula —NR'—C(O)—R, wherein R' is hydrogen or alkyl as indicated above, and R is cycloalkyl as indicated above.

The term "cycloalkenylcarbonylamino" is intended to indicate a radical of the formula —NR'—C(O)—R, wherein R' is hydrogen or alkyl as indicated above, and R is cycloalkenyl as indicated above.

The term "heterocycloalkylcarbonylamino" is intended to indicate a radical of the formula —NR'—C(O)—R, wherein R' is hydrogen or alkyl as indicated above, and R is heterocycloalkyl as indicated above.

The term "ureido" is intended to indicate a radical of the formula "—NR'—C(O)—NH—R, wherein R' is hydrogen or alkyl as indicated above, and R is hydrogen, alkyl, alkenyl, alkynyl, cycloalkyl or aryl as indicated above.

The term "thioureido" is intended to indicate a radical of the formula "—NR'—C(S)—NH—R, wherein R' is hydrogen or alkyl as indicated above, and R is hydrogen, alkyl, or cycloalkyl as indicated above.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroacetic, choline, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, ammonia, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylene-diamine, and dibenzylamine, or L-arginine or L-lysine.

The term "pharmaceutically acceptable in vivo hydrolysable ester" is intended to indicate easily in vivo hydrolysable esters, i.e. in vivo hydrolysable esters of the compounds of formula I such as alkanoyloxyalkyl, aralkanoyloxyalkyl, aroyloxyalkyl, e.g. acetoxymethyl, pivaloyloxymethyl, benzoyloxymethyl esters and the corresponding 1'-oxyethyl derivatives, or alkoxycarbonyloxyalkyl esters, e.g. methoxycarbonyloxymethyl esters and ethoxycarbonyloxymethyl esters and the corresponding 1'-oxyethyl derivatives, or lactonyl esters, e.g. phthalidyl esters, or dialkylaminoalkyl esters, e.g. dimethylaminoethyl esters. Such esters may be prepared by conventional methods known to persons skilled in the art, such as method disclosed in GB patent No. 1 490 852 incorporated herein by reference.

Compounds of formula I may comprise asymmetrically substituted (chiral) carbon atoms and carbon-carbon double bonds which may give rise to the existence of isomeric forms, e.g. enantiomers, diastereomers and geometric isomers. The present invention includes all such isomers, either in pure form or as mixtures thereof. Pure stereoisomeric forms of the compounds and the intermediates of this invention may be obtained by the application of procedures known in the art. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chirally pure starting materials. Likewise, pure geometric isomers may be obtained from the corresponding pure geometric isomers of the appropriate starting materials. A mixture of geometric isomers will typically exhibit different physical properties, and they may thus be separated by standard chromatographic techniques well-known in the art.

The present invention further includes prod rugs of compounds of general formula I, such as esters, ethers, complexes or other derivatives which undergo a biotransformation in vivo before exhibiting their pharmacological effects.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Embodiments

In one embodiment of the present invention the compounds of the present invention represent compounds according to formula Ia

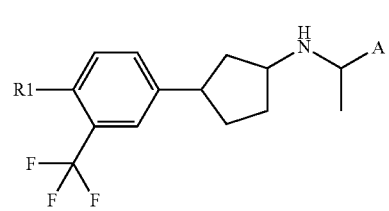

In another embodiment of the present invention the compounds of the present invention represent compounds according to formula Ib,

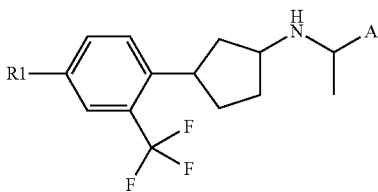

In another embodiment of the present invention, $R_2$ represents hydrogen.

In another embodiment of the present invention, $R_1$ represents halogen, cyano, —$NH_2$, carboxy, hydroxy, —C(O)H, oxo, hydroxymethyl, $C_{1-4}$alkoxy, $C_{1-4}$amino, mercapto, —C(O)$NH_2$, nitro, carboxy$C_{1-4}$alkoxy, $C_{1-4}$alkoxycarbonyl, $C_{1-4}$alkoxycarbonyl$C_{1-4}$alkoxy, carboxy$C_{1-4}$alkyl, $C_{1-4}$alkoxycarbonyl$C_{1-4}$alkyl, $C_{1-4}$alkylcarbonyl, $C_{1-4}$aminocarbonyl, hydroxyaminocarbonyl, $C_{3-6}$cycloalkylaminocarbonyl, $C_{1-5}$heterocycloalkylaminocarbonyl, $C_{3-6}$cycloalkylamino, $C_{1-5}$heterocycloalkylcarbonyl, $C_{6-10}$aryl, $C_{3-9}$heteroaryl, $C_{1-5}$heteroarylaminocarbonyl, —S(O)$_2NH_2$, $C_{1-4}$ureido, $C_{1-4}$thioureido, $C_{1-4}$alkylcarbonyloxy, $C_{1-6}$alkoxycarbonyloxy, $C_{1-4}$alkoxysulfonyloxy, $C_{1-5}$heterocycloalkyloxy, $C_{1-4}$aminosulfonyl, $C_{1-4}$aminocarbonyloxy, $C_{1-4}$alkylsulfonylamino, $C_{1-4}$alkylsulfonylamino$C_{1-3}$ alkyl, $C_{6-10}$arylamino, $C_{6-10}$arylaminocarbonyl, $C_{6-10}$aryloxycarbonyl, $C_{1-3}$alkoxycarbamoyl, $C_{6-10}$arylcarbonylamino, $C_{6-10}$arylsulfonylamino, $C_{1-4}$alkylcarbonylamino, $C_{1-3}$alkylcarbonylaminomethyl, $C_{2-4}$alkenylcarbonylamino; $C_{3-6}$cycloalkenylcarbonylamino, $C_{3-6}$cycloalkylcarbonylamino, $C_{1-4}$alkoxycarbonylamino, $C_{1-5}$heterocycloalkylcarbonylamino, $C_{1-4}$alkylsulfonyl, $C_{1-5}$heterocycloalkylsulfonyl or $C_{1-4}$alkylsulfonylaminocarbonyl, iminomethyl, hydroxyiminomethyl, amidino, trifluoromethyl, $C_{1-5}$alkyl, $C_{2-4}$alkenyl, $C_{2-4}$alkynyl, $C_{1-4}$hydroxyalkyl, amino$C_{1-4}$alkyl, $C_{1-4}$haloalkyl, $C_{3-6}$cycloalkyl, $C_{3-6}$cycloalkenyl, $C_{1-5}$heterocycloalkyl or $C_{2-5}$heterocycloalkenyl.

In yet another embodiment of the present invention $R_1$ represents hydroxy, $C_{1-4}$alkyl or $C_{1-4}$alkoxy, wherein said $C_{1-4}$alkyl or $C_{1-4}$alkoxy is optionally substituted with carboxy or $C_{1-4}$alkoxycarbonyl.

In a further embodiment of the present invention, $R_1$ represents carboxyethyl, hydroxy, carboxymethoxy, carboxyIsopropoxy, methoxycarbonylethyl, or ethoxycarbonylethyl.

In a further embodiment of the present invention, A represents $C_{6-10}$aryl optionally further substituted with one or more, same or different substituents represented by halogen, hydroxy, trifluoromethyl, cyano, carboxy, —C(O)H, —$NH_2$, —C(O)$NH_2$, $C_{2-6}$alkenyl, $C_{2-6}$alkynyl, $C_{1-6}$hydroxyalkyl, $C_{1-4}$alkoxy or phenyl.

In a further embodiment of the present invention, A represents naphthyl or phenyl, wherein said naphthyl or phenyl is optionally substituted with one or more, same or different substituents represented by halogen, hydroxy, trifluoromethyl, cyano, carboxy, —$NH_2$, $C_{1-6}$alkyl, $C_{1-6}$hydroxyalkyl, $C_{1-6}$haloalkyl or $C_{1-4}$alkoxy, such as fluoro, bromo, chloro, hydroxy, trifluoromethyl, cyano, carboxy, —$NH_2$, $C_{1-3}$alkyl, $C_{1-3}$hydroxyalkyl, $C_{1-3}$haloalkyl or $C_{1-3}$alkoxy.

In a further embodiment of the present invention, A represents naphthyl, 4-fluoro-3-methoxy-phenyl or 4-fluoro-2-methoxy-phenyl.

In yet an embodiment of the present invention, A represents $C_{6-10}$aryl, optionally substituted with one or more substituents represented by halogen or $C_{1-4}$alkoxy; $R_2$ represents hydrogen and $R_1$ represents hydroxy, $C_{1-4}$alkoxycarbonyl$C_{1-4}$ alkyl, carboxy$C_{1-4}$ alkoxy or carboxy$C_{1-4}$alkyl.

Specific examples of compounds of formula I may be selected from the group consisting of 3-{4-[(1R,3R)-3-((R)-1-naphthalen-1-yl-ethylamino)-cyclopentyl]-2-trifluoromethyl-phenyl}-propionic acid methyl ester, 3-{4-[(1R,3S)-3-((R)-1-naphthalen-1-yl-ethylamino)-cyclopentyl]-2-trifluoromethyl-phenyl}-propionic acid methyl ester, 3-{4-[(1S,3S)-3-((R)-1-naphthalen-1-yl-ethylamino)-cyclopentyl]-2-trifluoromethyl-phenyl}-propionic acid methyl ester, 3-{4-[(1S,3R)-3-((R)-1-naphthalen-1-yl-ethylamino)-cyclopentyl]-2-trifluoromethyl-phenyl}-propionic acid methyl ester, 3-{4-[(1R,3R)-3-((R)-1-naphthalen-1-yl-ethylamino)-cyclopentyl]-2-trifluoromethyl-phenyl}-propionic acid, 3-{4-[(1R,3S)-3-((R)-1-naphthalen-1-yl-ethylamino)-cyclopentyl]-2-trifluoromethyl-phenyl}-propionic acid, 3-{4-[(1S,3S)-3-((R)-1-naphthalen-1-yl-ethylamino)-cyclopentyl]-2-trifluoromethyl-phenyl}-propionic acid, 3-{4-[(1S,3R)-3-((R)-1-naphthalen-1-yl-ethylamino)-cyclopentyl]-2-trifluoromethyl-phenyl}-propionic acid, 3-(4-{(1S,3R)-3-[(R)-1-(4-fluoro-3-methoxy-phenyl)-ethylamino]-cyclopentyl}-2-trifluoromethyl-phenyl)-propionic acid methyl ester, 3-(4-{(1S,3S)-3-[(R)-1-(4-fluoro-3-methoxy-phenyl)-ethylamino]-cyclopentyl}-2-trifluoromethyl-phenyl)-propionic acid methyl ester, 3-[4-[(1S,3R)-3-[[(1R)-1-(4-fluoro-3-methoxy-phenyl)ethyl]amino]cyclopentyl]-2-(trifluoromethyl)phenyl]propionic acid, 3-[4-[(1S,3S)-3-[[(1R)-1-(4-fluoro-3-methoxy-phenyl)ethyl]amino]cyclopentyl]-2-(trifluoromethyl)phenyl]propanoic acid, 3-[4-[(1S,3S)-3-[[(1R)-1-(4-fluoro-2-methoxy-phenyl)ethyl]amino]cyclopentyl]-2-(trifluoromethyl)phenyl]propanoic acid, 3-[4-[(1S,3R)-3-[[(1R)-1-(4-fluoro-2-methoxy-phenyl)ethyl]amino]cyclopentyl]-2-(trifluoromethyl)phenyl]propanoic acid, ethyl 3-[4-[(1R,3R)-3-[[(1R)-1-(4-fluoro-3-methoxy-phenyl)ethyl]amino]cyclopentyl]-2-(trifluoromethyl)phenyl]propanoate, ethyl 3-[4-[(1R,3S)-3-[[(1R)-1-(4-fluoro-3-methoxy-phenyl)ethyl]amino]cyclopentyl]-2-(trifluoromethyl)phenyl]propanoate, 3-[4-[(1R,3S)-3-[[(1R)-1-(4-fluoro-3-methoxy-phenyl)ethyl]amino]cyclopentyl]-2-(trifluoromethyl)phenyl]propanoic acid, 3-[4-[(1R,3R)-3-[[(1R)-1-(4-fluoro-3-methoxy-phenyl)ethyl]amino]cyclopentyl]-2-(trifluoromethyl)phenyl]propanoic acid, 4-[(1S)-3-[[(1R)-1-(4-fluoro-3-methoxy-phenyl)ethyl]amino]cyclopentyl]-2-(trifluoromethyl)phenol (mixture of two diastereomers), 2-[4-[(1S)-3-[[(1R)-1-(4-fluoro-3-methoxy-phenyl)ethyl]amino]cyclopentyl]-2-(trifluoromethyl)phenoxy]-2-methyl-propanoic acid (mixture of two diastereomers), 2-[4-[(1S)-3-[[(1R)-1-(4-fluoro-3-methoxy-phenyl)ethyl]amino]cyclopentyl]-2-(trifluoromethyl)phenoxy]acetic acid (mixture of two diastereomers), 2-[3-[(1R)-3-[[(1R)-1-(4-fluoro-3-methoxy-phenyl)ethyl]amino]-cyclopentyl]-5-(trifluoromethyl)phenoxy]acetic acid, {3-[(1R,3R/S)-3-((1R)-1-Naphthalen-1-yl-ethylamino)-cyclopentyl]-5-trifluoromethyl-phenoxy}-acetic acid, or
3-[5-[(1R)-3-[[(1R)-1-(1-naphthypethyl]amino]cyclopentyl]-2-(trifluoromethyl)phenyl]propanoic acid.

Specific examples of intermediates for the preparation of compounds of formula I may be selected from the group consisting of
3-[4-(4,4,5,5-tetramethyl-[1,3,2]dioxaborolan-2-yl)-2-trifluoromethyl-phenyl]-acrylic acid methyl ester,
3-[4-(4,4,5,5-tetramethyl-[1,3,2]dioxaborolan-2-yl)-2-trifluoromethyl-phenyl]-propionic acid methyl ester,
rac-3-[4-(3-oxo-cyclopentyl)-2-trifluoromethyl-phenyl]-propionic acid methyl ester,
3-[4-((1S)-3-oxo-cyclopentyl)-2-trifluoromethyl-phenyl]-propionic acid methyl ester,
2-[4-bromo-3-(trifluoromethyl)phenyl]-4,4,5,5-tetramethyl-1,3,2-dioxaborolane,
(R)-3-(4-bromo-3-trifluoromethyl-phenyl)-cyclopentanone,
(R)-3-[4-(3-oxo-cyclopentyl)-2-trifluoromethyl-phenyl]-acrylic acid ethyl ester,
ethyl 3-[4-[(1R)-3-oxocyclopentyl]-2-(trifluoromethyl)phenyl]propanoate,
4-(4,4,5,5-tetramethyl-[1,3,2]dioxaborolan-2-yl)-2-trifluoromethyl-phenol, or
(S)-3-(4-hydroxy-3-trifluoromethyl-phenyl)-cyclopentanone,
Ethyl 2-[3-[(1R)-3-oxocyclopentyl]-5-(trifluoromethyl)phenoxy]acetate,
4-Bromo-2-iodo-1-trifluoromethyl-benzene,
3-(5-Bromo-2-trifluoromethyl-phenyl)-acrylic acid methyl ester,
3-[5-(4,4,5,5-Tetramethyl-[1,3,2]dioxaborolan-2-yl)-2-trifluoromethyl-phenyl]-acrylic acid methyl ester,
Methyl 3-(5-(4,4,5,5-tetramethyl-1,3,2-dioxaborolan-2-yl)-2-(trifluoromethyl)phenyl propanoate, or
3-[5-((1R)-3-Oxo-cyclopentyl)-2-trifluoromethyl-phenyl]-propionic acid methyl ester.

Pharmaceutical Compositions

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.05-99.9% by weight of the formulation.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, ophthalmic, transdermal, intra-articular, topical, pulmonary, nasal, buccal or rectal administration or in any other manner appropriate for the formulation of compounds used in nephrology and in accordance with accepted practices such as those disclosed in *Remington: The Science and Practice of Pharmacy*, 21$^{st}$ ed., 2000, Lippincott Williams & Wilkins. In the composition of the invention, the active component may be present in an amount of from about 0.01 to about 99%, such as 0.1% to about 10% by weight of the composition.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula I is dispersed evenly throughout the composition so that the composition may readily be subdivided into equally effective unit dosage forms such as tablets or capsules. The preformulation composition may then be subdivided into unit dosage forms containing from about 0.05 to about 1000 mg, in particular from about 0.1 to about 500 mg, e.g. 10-200 mg, such as 30-180 mg, such as 20-50 mg of the active compound of the invention.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dose is administered at once) or in divided doses two or more times a day.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds. The administration of a compound of the present invention with one or more other active compounds may be either concomitantly or sequentially.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use.

The composition intended for parenteral administration may additionally comprise conventional additives such as stabilisers, buffers or preservatives, e.g. antioxidants such as methyl hydroxybenzoate or the like.

Compositions for rectal administration may be in the form of a suppository incorporating the active ingredient and a carrier such as cocoa butter, or in the form of an enema.

Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-in-oil emulsions such as creams, ointments or pastes; or solutions or suspensions such as drops. For topical administration, the compound of formula I may typically be present in an amount of from 0.01 to 20% by weight of the composition, such as 0.1% to about 10%, but may also be present in an amount of up to about 50% of the composition. Compositions for ophthalmic treatment may preferably additionally contain a cyclodextrin. Compositions suitable for administration to the nasal or buccal cavity or for inhalation include powder, self-propelling and spray formulations, such as aerosols and atomizers. Such compositions may comprise a compound of formula I in an amount of 0.01-20%, e.g. 2%, by weight of the composition.

The composition may additionally comprise one or more other active components conventionally used in the treatment of physiological disorders or diseases associated with disturbances of CaSR activity, such as hyperparathyroidism.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosage is administered at once) or in divided doses two or more times a day.

Pharmacological Methods

The calcium sensing receptor (CaSR) and its use in identifying or screening for calcimimetic compounds has been described in EP 637 237, EP 1 296 142, EP 1 100 826, EP 1 335 978, and EP 1 594 446.

In vitro and vivo methods for testing the compounds of the present invention are well established and may be found in the references listed above, or e.g. in Journal of Biological Chemistry (2004), 279(8), 7254-7263 or in U.S. Pat. No. 5,858,684 and references cited therein.

Biological Assay for Analysis of In Vitro Activity

The assay investigates a compound's functional ability to act as a biological positive modulator on the human CaSR. Activation of the receptor expressed on CHO-K1 cells is detected through the G alpha q pathway, the activation of phospholipase C and the accumulation of intracellular inositol phosphate (IP) as described earlier [Sandrine Ferry, Bruno Chatel, Robert H. Dodd, Christine Lair, Danielle Gully, Jean-Pierre Maffrand, and Martial Ruat. *Effects of Divalent Cations and of a Calcimimetic on Adrenocorticotropic Hormone Release in Pituitary Tumor Cells*. BIOCHEMICAL AND BIOPHYSICAL RESEARCH COMMUNICATIONS 238, 866-873 (1997)]. The human CaSR is stably expressed on a CHO-K1 cell clone, stimulated with a basal level of calcium and challenged with the tested compound. The level of IP1 is determined using the IP-One htrf kit (Cisbio, France). CHO-K1 cells not transfected with the CaSR fail to elicit an IP1 response upon calcium and/or compound stimulation.

Cloning of the Human CaSR Gene

The ORF coding for the human CaSR (genebank: NM_000388) was acquired from Invitrogen Corp, USA and subsequently cloned into the mammalian expression vector pCDA3.1.

Generation of Cell Line Expressing CaSR

CHO-K1 cells were transfected using Lipofectamine according to manufacturer's protocol (400.000 cells/well were seeded in a 6-well plate and transfected after 24 hours using 2 µg DNA and 5 µl lipofectamine). After another 24 hours the cells were detached, seeded and subjected to 1 mg/ml of G-418. Following 7 days growth single clones were picked, the CaSR expression evaluated using the 5C10 antibody against CaSR, the clones with the highest expression were selected and tested for functional response. The preferred clone was continuously cultured according to standard procedures described in ATCC (American Type Culture Collection) protocols for CHO-K1 with the addition of 500 µg/ml G-418.

Functional Whole Cell Assay

On the assay day cells were harvested and resuspended to $13*10^6$ cells/ml in stimulation buffer (containing: Hepes 10 mM, $MgCl_2$ 0.5 mM, KCl 4.2 mM, NaCl 146 mM, glucose 5.5 mM, LiCl 50 mM at pH 7.4). Five µl cell solution were pipetted into a well (white 384-well plate, Perkin Elmer Optiplate) followed by 5 µl compound diluted in a $Ca^{2+}$-containing (to the final concentration of 2 mM) buffer. After compound stimulation for 1 hour at 37° C. 10 µl of IP-One assay reagents were added and incubated for another 1 hour at room temperature. Finally the plate was read using a Perkin Elmer EnVision, according to protocol supplied by the IP-One assay kit manufacturer. The FRET ratio was calculated by dividing the 665 nm emission signal with that of the 615 nm.

Testing data of compounds of the present invention indicate that compounds of the present invention are potent modulators of CaSR, thus making them potentially useful in the treatment of diseases related to kidneys or bones.

As described above, the compounds described in the present invention are modulators of CaSR activity. The CaSR can be found in the parathyroid gland, the thyroid, bone cells, the stomach, the lung, the kidney, pituitary gland, the brain, the hypothalamus, the olfactory areas or the hippocampus. Compounds according to the present invention may preferably be more selective, in their use, with respect to the receptors of the parathyroid compared with those of the thyroid gland.

The compounds according to the invention, and the pharmaceutical compositions comprising them, may be used as a medicinal product, in particular for the treatment of physiological disorders or diseases associated with disturbances of CaSR activity. Even more particularly, these physiological disorders or diseases of the type including primary or secondary hyperparathyroidism, osteoporosis, cardiovascular, gastrointestinal, endocrine or neurodegenerative diseases or certain cancers in which $(Ca^{2+})_e$ ions are abnormally high. The secondary hyperparathyroidism is more particularly observed in chronic renal failure.

Screening for P450 2D6 Inhibition

The assay rapidly screen for potential inhibitors of human P450 2D6 catalytic activity, by using recombinant human P450 2D6. The IC50 determination is performed in duplicate at eight concentrations.

Incubations were conducted in 96 well microtiter plates based on a method described by BD Biosciences. To the first well in each row, a NADPH regenerating system and test compound was added. In the second well and all remaining wells, NADPH regenerating system and acetonitrile (final concentration of 2%) was added. The final assay concentration of the NADPH regenerating system was 8.2 µM NADP+, 0.41 mM glucose-6-phosphate, 0.41 mM magnesium chloride hexahydrate and 0.4 U/ml glucose-6-phosphate dehydrogenase and 0.01 mg/mL control insect cell membrane protein. The test compound solution was serially diluted 1:3 through the eighth wells. The final concentration of the test compounds were in the range 100 µM to 45.7 nM in the eight rows. Wells 9 and 10 contained no test compound (only NADPH regenerating system and enzyme/substrate mix) and wells 11 and 12 were used as controls for background fluorescence (enzyme and substrate were added after the reaction was terminated). The plate was then pre-incubated at 37° C. for 10 min, and the reaction was initiated by the addition of pre-warmed enzyme/substrate mix. The assay concentration of the enzyme/substrate mix was 100 mM potassium phosphate, pH 7.4, 1.5 pmol recombinant human P450 CYP2D6 and 1.5 µM of the fluorescent substrate 3-[2-(N,N diethyl-N-methylamino)ethyl]-7-methoxy-4-methylcoumarin (AMMC). The assay was conducted in duplicate in a final volume of 200 µL per well. Reactions were terminated after 30 min by addition of a 4:1, acetonitrile:0.5 M Tris base solution. Quinidine was used as positive control, 0.5 µM as highest concentration. Fluorescence per well was measured using a fluorescence plate reader (excitation: 390 nm, emission: 460 nm). The IC50 values were calculated.

Test data of compounds of the present invention indicate that compounds of the present invention show low or no inhibition towards human P450 2D6 (pIC50-value below or equal to 6).

Biological Assay for Analysis of Clearance in Rat Hepatocytes

Test compound concentration is 0.5 µM and cell concentration is 1×10⁶ cells/mL in the incubation. The described method is manual and is based on a 24-well format.

The liver is collected from a male Spraque-Dawley rat. One liver lobe is cut off and flushed with various buffers to loosen the cells. The cell suspension is washed and centrifuged, and the cell density is adjusted to 1.2×10⁶ cells/mL with Krebs-Henseleit buffer, pH 7.4, containing 0.2% bovine serum albumin (BSA). Only cell suspensions with viability above 80% are used.

Incubation Conditions

A volume of 315 µL cell suspension per well is added to 24-well plates and preincubated at 37° C. for 20 min. Test compound (0.5 µM) is added, and the mixture is incubated for 20 minutes. Incubations are run in duplicate. Samples are withdrawn at predetermined stop times and mixed with methanol containing internal standard (IS) to terminate all enzyme activity and precipitate proteins.

The percentage of organic solvent in the incubations is less than 1%. Careful inspections of reagents are performed prior to the start of any experiment to ensure all reagents are in solution.

Sample Analysis

The 24-well plates are centrifuged. Test compound depletion, using a compound specific LC/MS/MS method, is determined. The logarithm of the peak area ratios of test compound to internal standard (IS) versus incubation time is plotted in a graph The rate constant (k) (min⁻¹) of test compound depletion is calculated from the linear part of the curve and the half-time ($t_{1/2}$) in minutes can be calculated from the rate constant (Eq. 1).

$$t_{1/2} = (\ln 2)/k \quad (Eq. 1)$$

Intrinsic clearance ($Cl_{int}$) (mL/min/10⁶ cells) is calculated from:

$$Cl_{int} = k/c \quad (Eq. 2)$$

where c is the cell concentration in 10⁶ cells/mL.

Conversion to apparent clearance ($Cl_{app}$) (mL/min/kg) is done by Eq. 3:

$$Cl_{app} = Cl_{int} \times a \times b/d \quad (Eq. 3)$$

where a, b and d are the scaling factors for normalizing $Cl_{int}$ to rat body weight.

The following rat scaling factors are used:
a: 120 (cells/liver weight (10⁶ cells/g))
b: 10 (liver weight (g))
d: 0.25 (body weight (kg))

Apparent clearance is a measure of compound elimination from the liver. Apparent clearance below approximately 25 mL/min/kg rat body weight (corresponding to extraction ratio of approx. 30%) is considered as low clearance (high metabolic stability). Apparent clearance above approximately 165 mL/min/kg rat body weight (corresponding to extraction ratio of approx. 75%) is considered as high clearance (low metabolic stability).

Testing data of compounds of the present invention indicate that compounds of the present invention show low metabolic clearance in rat hepatocytes (<55 mL/min/kg, corresponding to extraction.ratio of approx. 50%). See table 1.

TABLE 1

CaSR modulation data and pharmacokinetic data for compounds of the present invention.

| Compound no. | Functional whole cell assay (modulation of human CaSR) A: <500 nM; B: 500-2000 nM; C: 2-5 µM | Clearance ($Cl_{app}$) in rat hepatocytes A: <30 mL/min/kg; B: 30-55 mL/min/kg; C: >55 mL/min/kg |
|---|---|---|
| 1007 | A | B |
| 1012 | A | A |
| 1021 | A | A |
| 1022 | A | A |
| 1023 | A | B |

The test data of the compounds of the present invention indicate that the presence of a trifluoromethyl functional group modulates the in vitro metabolic stability of the compounds relative to compounds lacking the trifluoromethyl, in the sense that the in vitro clearance of the compounds of the present invention in e.g. rat hepatocytes is increased, which may lead to improved in vivo pharmacokinetic properties such as increased bioavailability, exposure and half-life.

The invention is described in further detail in the following non-limiting examples which are not in any way intended to limit the scope of the invention as claimed.

Abbreviations

The following standard abbreviations are used throughout this disclosure:
Ac=acetyl
Acac=acetylacetone
aq.=aqueous
BINAP=2,2'-bis(diphenylphosphino)-1,1'-binaphthyl
Bu=n-butyl
COD=cyclooctadiene
dba=dibenzylideneacetone
DCC=dicyclohexylcarbodiimide
DCM=dichloromethane
DIPEA=diisopropyl ethylamine
DMF=dimethylformamide
DMSO=Dimethyl sulfoxide
eq.=equivalent
Et=ethyl
EtOAc=ethyl acetate
h=hour(s)
HPLC/MS=High Performance Liquid Chromatography/Mass Spectrometry
i-Pr=isopropyl
LG=Leaving group
NADPH=reduced Nicitinamide adenine dinucleotide phosphate
Me-DuPHOS=1,2-bis-(2,5-dimethylphospholano) benzene
MTBE=methyl tert-butyl ether
nbd=norbornadiene
$NEt_3$=triethylamine
o-Tol=ortho-tolyl
$PCy_3$=tricyclohexylphosphine
Pd/C=Palladium on carbon
Pt/C=Platinium on carbon
THF=tetrahydrofuran
rt=room temperature
RT=retention time Methods of Preparation The compounds of general formula I can be prepared in a number of ways well known to those skilled in the art of organic synthesis. The compounds of formula I can be synthesised using the methods outlined below, together with methods known in the art of synthetic organic chemistry, or variations thereof as appreciated by those skilled in the art. Preferred methods include, but are not limited to, those described below.

The compounds of formula I can be prepared by techniques and procedures readily available to one of ordinary skill in the art, for example by following the procedures as set forth in the following schemes. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionalities present on various portions of the starting molecules in a reaction must be compatible with the reagents and reactions proposed. Not all compounds of formula I falling into a given class may be compatible with some of the reaction conditions required in some of the methods described. Such restrictions to the substituents which are compatible with the reaction conditions will be readily apparent to one skilled in the art and alternative methods can be used.

The schemes described in this section are not intended to limit the scope of the invention in any way. All substituents, unless otherwise indicated, are previously defined. The reagents and starting materials are either available from commercial suppliers or prepared by methods known to one of ordinary skill in the art following procedures set forth in references such as *Fieser and Fieser's Reagents for Organic Synthesis*, Volumes 1-22 (John Wiley and Sons, 2004); *Rodd's Chemistry of Carbon Compounds*, Volumes 1-5 and Supplements (Elsevier Science Publishers, 2000); *Organic Reactions*, Volumes 1-64 (John Wiley and Sons, 2004); *March's Advanced Organic Chemistry* (John Wiley and Sons, 5$^{th}$ Edition) and *Larock's Comprehensive Organic Transformations* (VCH Publishers Inc., 1999). These schemes are merely illustrative of some methods by which the compounds of this invention can be synthesised, and various modifications to these schemes can be made and will be suggested to one skilled in the art having referred to this disclosure. The starting materials and the intermediates of the reactions may be isolated and purified if desired using conventional techniques, including but not limited to filtration, distillation, crystallisation, chromatography and the like. Such materials may be characterised using conventional means, including physical constants and spectral data.

Compounds of general formula I-may be obtained by reductive amination between a cyclopentanone of general formula II and an amine of general formula III. The reaction between ketone II and amine III may be carried out either by one-pot reductive amination or with isolation of the imine followed by reduction.

a. The formation of the intermediate iminium IV may be promoted by addition of a protic or aprotic acid such as, but not limited to acetic acid and Ti(Oi-Pr)$_4$ respectively.

The reducing agent may be but is not limited to Na(CN)BH$_3$, NaBH$_4$, Na(OAc)$_3$BH (for other non-limiting conditions see *Org. React.* 2002, 59, 1-714 and references cited therein).

b. The formation of the imine is promoted either by Lewis acids such as TiCl$_4$, ZnCl$_2$, AlCl$_3$ or by bases such as pyridine, optionally in the presence of a drying agent such as TiCl$_4$ or molecular sieve (see *Comprehensive Organic Functional Group Transformations* 3, 403 (1995) Pergamon).

c. Reduction may be performed by hydrogenation in the presence of a catalyst such as Pd/C, Pt/C or a chiral rhodium complex to perform the reaction in a stereoselective manner or by hydride transfer from a reducing agent such as BH$_3$, NaBH$_4$, NaBH$_3$CN, LiAlH$_4$, L-selectride (see Larock R. C. *Comprehensive Organic Transformations* 1989, VCH; *Comprehensive Organic Functional Group Transformations* 2, 268-269 (2005) Pergamon and references cited therein).

Compounds of general formula I may also be prepared through alkylation of the amine III.

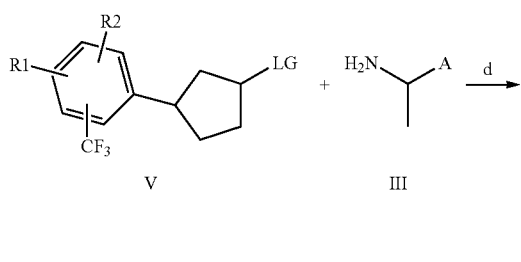

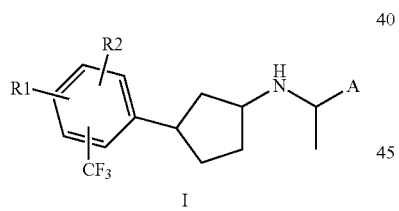

LG = leaving group d. When LG is a leaving group such as chloride, bromide, iodide, tosylate or triflate, alkylation is performed in the presence of a base such as NEt$_3$, DIPEA, NaH, NaOH, KOH, carbonates in an appropriate solvent such as DMF, pyridine, DMSO, CH$_3$CN, acetone, toluene. Alternatively reaction with an alcohol (LG=OH) may also be considered. Such Mitsunobu-like reaction is performed in the presence of a phosphine such as PBu$_3$, PPh$_3$ and the like, an azodicarboxylate or an azodicarboxamide in an aprotic solvent, typically THF. For this purpose the amine III is protected/activated as a carbamate or a sulphonamide. The resulting compound is deprotected using standard conditions (*Protective Groups in Organic Synthesis*, T. W. Greene and P. G. M. Wuts, John Wiley and Sons, 3$^{rd}$ Edition 1999 and reference sited therein) to afford I.

The cyclopentanone II may be prepared in various manners:

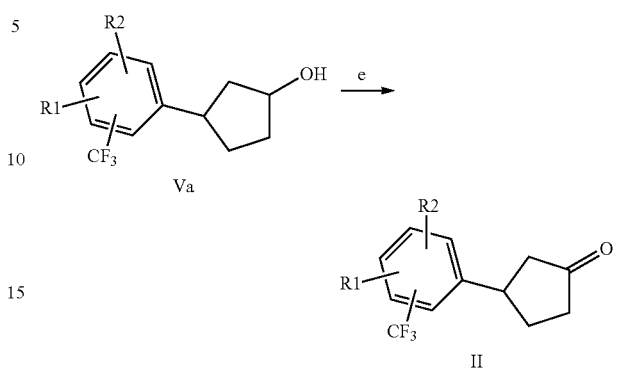

e. An alcohol Va may be oxidised to afford II. Oxidation may be performed with many different reagents. A few of them are H$_2$Cr$_2$O$_7$, Acetone/Al$_2$O$_3$, MnO$_2$, periodinanes, DMSO in combination with DCC, acetic anhydride, oxalyl chloride and the like.

2-Cyclopentenones may be used as starting materials.

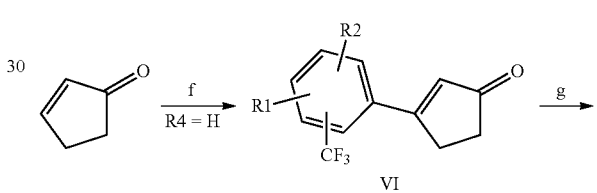

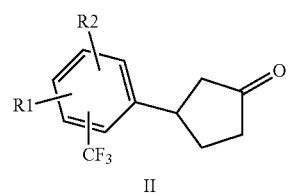

f. Coupling reaction with an arylhalide or pseudo halide such as triflate in the presence of a palladium source such as Pd(OAc)$_2$, PdCl$_2$(PPh$_3$)$_2$, a base such as NEt$_3$, K$_2$CO$_3$, NaHCO$_3$, optionally with a phosphine such PPh$_3$, P(o-Tol)$_3$, 1,3-bis(diphenylphosphino)propane (dppp), optionally in the presence of a salt like NBu$_4$Cl, AgNO$_3$ in a solvent such as DMF or acetonitrile. Alternatively a decarboxylative Heck-type coupling may be performed using an aryl/heteroaryl carboxylic acid (*Org. Lett.* 2004, 6, 433).

g. Chemospecific reduction of the double bond may be performed under numerous conditions. The hydrogen source may be H$_2$, water, Hantzsch esters. Metal-based catalysts such as Pd/C, Pd(PPh$_3$)$_4$, supported PdCl$_2$, Rh-, Co-, Cu-, Ir-based catalysts may be used. Stereoselectivity may be achieved by addition of a chiral auxiliary such as but not limited to enantiopure binaphtol phosphate derivatives/valine, imidazolidinone iminiums, bidentate phosphines.

Alternatively 2-cyclopentenones may be subjected to 1,4-addition.

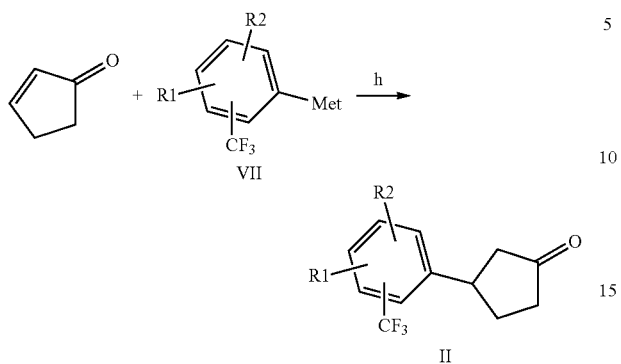

h. Reaction with an aryl metal VII in which Met may be Li, Mg halide, trialkyltin, boronic acid, boronic acid ester, optionally in the presence of a metal complex such as PdCl$_2$, Pd(OAc)$_2$, Pd(PPh$_3$)$_4$, (acac)Rh(CO)$_2$, Ni(acac)$_2$, (COD)Rh(1,4-dihydroquinone)BF$_4$ with a ligand typically phosphine-based such as PBu$_3$, PPh$_3$, 1,3-bis(diphenylphosphino)propane (dppp), 1,3-hydroquinone or 1,4-hydroquinone in solvents such as DMF, THF, water, toluene, dioxane, dimethoxyethane. In the presence of a chiral ligand as a pure enantiomer such as BINAP, phosphoramidite, Me-DuPHOS and the like the reaction may be performed stereoselectively.

3-Methoxy-cyclopent-2-enone may be used as a starting material.

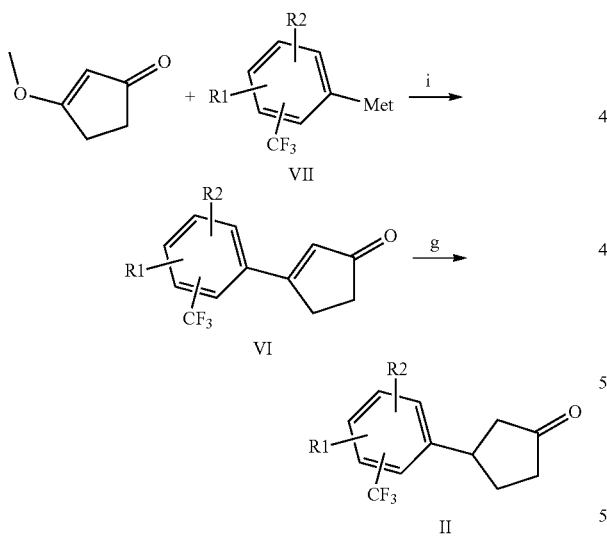

i. Addition of an organometallic species VII (Met=Li or MgHal (Hal=Cl, Br)) affords cyclopentenone VI. The cyclopentenone VI may then be transformed to cyclopentanone II as described above.

j. The aryl metal species VII in which Met=Li or MgHal may be prepared from the corresponding aryl halides IX by metallation using n-butyl lithium, t-butyl lithium, Li, Mg, i-propyl magnesium chloride in solvents such as diethyl ether, THF. Aryl metal species VII in which Met=boronic acid ester may be prepared by cross-coupling of aryl halides IX with e.g. 1,3,2-dioxaborolane in the presence of a catalyst such as Pd(OAc)$_2$, PdCl$_2$(PPh$_3$)$_2$, Pd(PPh$_3$)$_4$ and a base such as NEt$_3$, K$_2$CO$_3$, NaHCO$_3$ in solvents such as 1,4-dioxane, DMSO, DMF, THF, toluene, DCM. Aryl metal species VII in which Met=trialkyltin may be prepared from the corresponding lithiated species using e.g. trialkyltin chloride in solvents such as diethyl ether, THF. Alternatively, compounds VII (Met=trialkyltin) may be prepared from aryl halides IX and hexaalkyldistannane in the presence of a catalyst such as Pd(OAc)$_2$, PdCl$_2$(PPh$_3$)$_2$, Pd(PPh$_3$)$_4$ in solvents such as 1,4-dioxane, DMSO, DMF, THF, toluene, DCM.

k. Aryl halides of general formula IX may be prepared from the corresponding dihalogenated derivatives X by reaction with difluorodihalomethanes such as CF$_2$Br$_2$, CF$_2$Cl$_2$, and CF$_2$BrCl in N,N-dimethyl-acetamide in the presence of a catalyst such as copper(I)iodide, cadmium powder or zinc powder (J. Am. Chem. Soc. (1985), 107, 5014), or by reaction with a CF$_3$ source such as CF$_3$COOH (J. Med. Chem. (2008), 51, 1260-1277), CF$_3$Si(CH$_3$)$_3$ (Eur. J. Org. Chem. (2006), 19, 4398-4404) CF$_3$I (J. Med. Chem. (2007) 50, 4351-4373) in the presence of a catalyst such as copper(I)iodide, and in solvents such as DMF, pyridine, N,N-dimethyl-acetamide, or NMP.

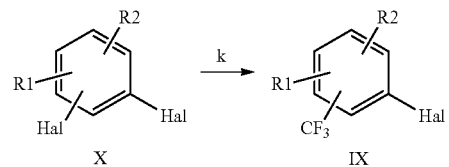

Ideally, the halogens in derivative X should be different, e.g. an iodide and a bromide, in order to obtain chemoselectivity.

Chiral amines of the general formula III are commercially available or may be prepared from the more readily available aldehydes by catalytic asymmetric synthesis using tert-butanesulfinamide according to Liu, G.; Cogan, D. A.; Ellmann, J. A., J. Amer. Chem. Soc., 1997, 114, 9913.

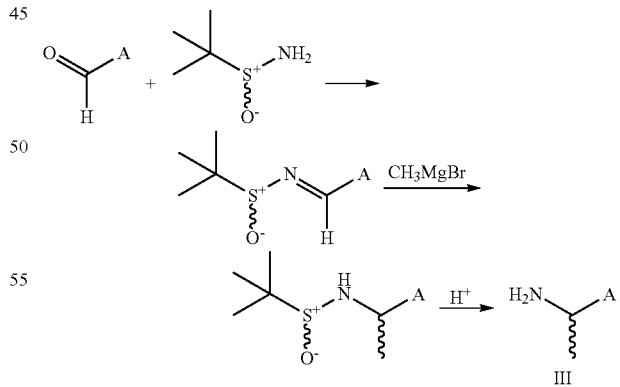

Many of the general methods described above may be used in a different order whenever appropriate.

EXAMPLES

The term "R/S" in the examples indicates a single configuration of a chiral atom for which the absolute stereochemistry has not been determined (either R or S). The absence of a stereochemical descriptor for a chiral atom indicates a mixture of isomers, in which both configurations of the atom are present (both R and S).

[Rh(R-BINAP)(nbd)]BF$_4$ was prepared according to the procedure described in Itooka, R.; Iguchi, Y.; Miyaura, N.; J. Org. Chem., 2003, 68, 6000. [Rh(S-BINAP)(nbd)]BF$_4$ was prepared following the same procedure, but using (S)-BINAP instead of (R)-BINAP.

General Procedure A

To a solution of ketone (1 eq.) in DMF (0.38M) were added the amine (1.1 eq.), glacial AcOH (1.2 eq.) and NaBH(OAc)$_3$ (1.4 eq.). The mixture was stirred at rt. overnight and filtered. Purification was performed by preparative HPLC-MS.

General Procedure B

To a solution/suspension of ester (6.5 mmol) in MeOH (30 mL) and water (10 mL) was added LiOH (5-8 eq.). After shaking/stirring for 4 h, the reaction mixture was concentrated slightly in vacuo, and additional water was added. The product was precipitated by adding 4N aq. HCl with stirring until pH 5 (to form the neutral compound) or pH 1-2 (to form the hydrochloride salt). Precipitates were collected by filtration. If no precipitation occurred, the mixture was extracted with DCM, the organic extracts were concentrated in vacuo, the residue was dissolved in DMSO and/or DMF, and the product was purified by preparative HPLC-MS.

Preparative HPLC/MS

Preparative HPLC/MS was performed on a Dionex APS-system with two Shimadzu PP150 prep. pumps and a Thermo MSQ Plus mass spectrometer. Column: Waters XBridge C-18, 150 mm×21.2 mm, 5 μm; solventsystem: A=50 mM Ammonium hydrogencarbonate and B=acetonitrile; flow rate=18 mL/min.

Analytical pre-analysis using the following method:

Column: Waters XBridge C-18, 150 mm×4.6 mm, 5 μm; method (10 min): Linear gradient method going from 10% B to 95% B in 6.5 minutes and staying at 95% B for another 1.5 minutes to obtain the retention time of the compounds provides the following four different preparative gradient methods:

0-3 min: 5% B for 2 minutes followed by a linear gradient method going from 5% B to 35% B in 4.5 minutes and going to 100% B and staying at 100% B for another 1.5 minutes.

3.01-5 min: 15% B for 1 minutes followed by a linear gradient method going from 15% B to 55% B in 5.5 minutes and going to 100% B and staying at 100% B for another 1.5 minutes.

5.01-7.5 min: 30% B for 1 minutes followed by a linear gradient method going from 30% B to 70% B in 5.5 minutes and going to 100% B and staying at 100% B for another 1.5 minutes.

7.51-10 min: 50% B for 1 minutes followed by a linear gradient method going from 50% B to 100% B in 5.5 minutes and staying at 100% B for another 1.5 minutes.

The fractions were collected based on ion traces of relevant ions and PDA signal (240-400 nm).

Analytical HPLC/MS

Analytical HPLC/MS was performed on a Dionex APS-system with a P680A analytical pump and a Thermo MSQ Plus mass spectrometer. Column: Waters XBridge C-18, 150 mm×4.6 mm, 5 im; solventsystem: A=50 mM Ammonium hydrogencarbonatend B=acetonitrile; flow rate=1.2 mL/min; method (8 min): Linear gradient method going from 10% B to 90% B in 4.5 minutes and staying at 90% B for another 1.5 minutes.

Preparation 1. 3-[4-(4,4,5,5-tetramethyl-[1,3,2]dioxaborolan-2-yl)-2-trifluoromethyl-phenyl]-acrylic acid methyl ester

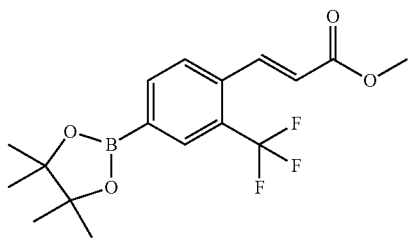

To a solution of 4-formyl-3-(trifluoromethyl)benzeneboronic acid (10 g) in dry THF (200 mL) was added 2,3-dimethyl-butane-2,3-diol (5.5 g) and 4 Å molecular sieves. After stirring at rt. for 5 hours, the mixture was filtered through Celite, which was washed with additional THF. To the filtrate was added methyl (triphenylphosphoranylidene)-acetate (16.3 g), and the mixture was stirred at rt for 2 hours. The solvent was removed in vacuo, the residue was suspended in diethyl ether (200 mL), and stirring was continued for 30 min, after which heptane (200 mL) was added. The suspension was filtered through a pad of silica gel, which was washed with additional diethyl ether/heptane 1:1 (200 mL). The filtrate was concentrated under reduced pressure to afford the title compound as a colorless oil, which was used without further purification. $^1$H NMR (300 MHz, DMSO) δ 8.08 (d, 1H), 8.01-7.80 (m, 3H), 6.79 (d, 1H), 3.77 (s, 3H), 1.32 (s, 12H).

Preparation 2. 3-[4-(4,4,5,5-tetramethyl-[1,3,2]dioxaborolan-2-yl)-2-trifluoromethyl-phenyl]-propionic acid methyl ester

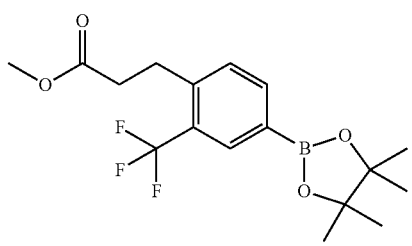

A solution of 3-[4-(4,4,5,5-tetramethyl-[1,3,2]dioxaborolan-2-yl)-2-trifluoromethyl-phenyl]-acrylic acid methyl ester (preparation 1) in ethyl acetate (200 mL) containing Pd/C (500 mg) was hydrogenated overnight at rt. The catalyst was filtered off through Celite, and the filtrate was concentrated under reduced pressure to afford the title compound as a colorless oil, which was used without further purification. $^1$H NMR (300 MHz, DMSO) δ 7.92-7.83 (m, 2H), 7.54 (d, 1H), 3.62 (s, 3H), 3.06 (t, 2H), 2.70-2.61 (m, 2H), 1.31 (s, 12H).

Preparation 3. rac-3-[4-(3-oxo-cyclopentyl)-2-trifluoromethyl-phenyl]-propionic acid methyl ester

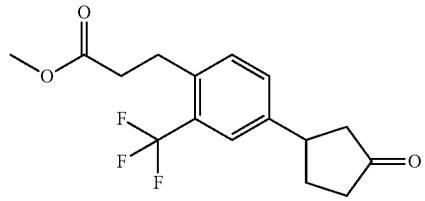 [SMILES: COC(=O)CCc1ccc(C2CCC(=O)C2)cc1C(F)(F)F]

To a solution of 3-[4-(4,4,5,5-tetramethyl-[1,3,2]dioxaborolan-2-yl)-2-trifluoromethyl-phenyl]-propionic acid methyl ester (preparation 2) (4.6 mmol) and [(1,4-hydroquinone)-rhodium(COD)]BF$_4$ (Son et al., *J. Am. Chem. Soc.* 2005, 127, 12238) (2 mol %) in water/dimethoxyethane (1:1, 20 mL, degassed) was added 2-cyclopenten-1-one (4.6 mmol) and LiOH (8 mol %). The mixture was warmed to 50° C. and stirred overnight. Additional water was added, and the mixture was extracted with dichloromethane. The organic phase was separated, dried and concentrated in vacuo to afford the title compound as a brown oil. $^1$H NMR (300 MHz, DMSO) δ 7.72-7.56 (m, 2H), 7.54-7.39 (m, 1H), 3.62 (s, 3H), 3.53-3.36 (m, 1H), 3.08-2.95 (m, 2H), 2.70-2.47 (m, 3H), 2.43-2.21 (m, 4H), 2.02-1.83 (m, 1H).

Example 1

3-{4-[(1S,3R)-3-((R)-1-naphthalen-1-yl-ethylamino)-cyclopentyl]-2-trifluoromethyl-phenyl}-propionic acid methyl ester, 3-{4-[(1R,3R)-3-((R)-1-naphthalen-1-yl-ethylamino)-cyclopentyl]-2-trifluoromethyl-phenyl}-propionic acid methyl ester, 3-{4-[(1S,3S)-3-((R)-1-naphthalen-1-yl-ethylamino)-cyclopentyl]-2-trifluoromethyl-phenyl}-propionic acid methyl ester, 3-{4-[(1R,3S)-3-((R)-1-naphthalen-1-yl-ethylamino)-cyclopentyl]-2-trifluoromethyl-phenyl}-propionic acid methyl ester (compounds 1001/1002/1003/1004)

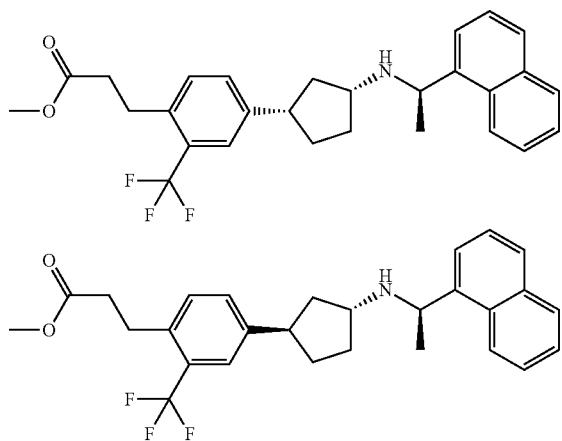

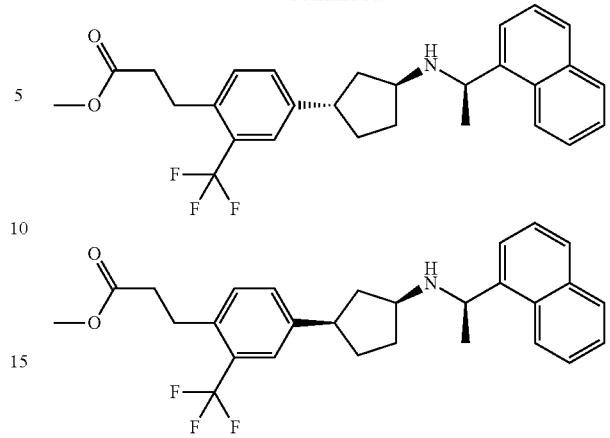

General procedure A was followed using rac-3-[4-(3-oxo-cyclopentyl)-2-trifluoromethyl-phenyl]-propionic acid methyl ester (preparation 3) as the ketone and (R)-1-naphthalen-1-yl-ethylamine as the amine. The resulting 4 diastereomers (title compounds) were isolated by preparative chiral HPLC. Preparative chiral HPLC was performed on a Chiralpak AD-H column 250×20 mm at 25° C., UV detection at 280 nm. Isocratic separation with ethanol:n-heptan:NEt$_3$:CH$_3$COOH (15:85:0.1:0.1); flow rate=17 mL/min. Compound 1001: RT=7.7. $^1$H NMR (300 MHz, DMSO) δ 8.34-8.24 (m, 1H), 7.96-7.87 (m, 1H), 7.82-7.69 (m, 2H), 7.58-7.44 (m, 5H), 7.39 (d, 1H), 4.71-4.60 (m, 1H), 3.61 (s, 3H), 3.09-2.86 (m, 4H), 2.61 (dd, 2H), 2.25-2.10 (m, 1H), 1.95-1.41 (m, 5H), 1.38 (t, 3H). Compound 1002:RT=9.4. $^1$H NMR (300 MHz, DMSO) δ 8.34-8.25 (m, 1H), 7.96-7.87 (m, 1H), 7.78 (d, 1H), 7.75-7.69 (m, 1H), 7.56-7.32 (m, 6H), 4.66 (q, 1H), 3.60 (s, 3H), 3.39-3.24 (m, 1H), 3.20-3.06 (m, 1H), 3.01-2.90 (m, 2H), 2.65-2.55 (m, 2H), 2.12-1.85 (m, 3H), 1.61-1.33 (m, 6H). Compound 1003: RT=10.6. $^1$H NMR (300 MHz, DMSO) δ 8.30 (d, 1H), 7.96-7.88 (m, 1H), 7.77 (d, 1H), 7.72 (d, 1H), 7.57-7.45 (m, 3H), 7.41-7.32 (m, 3H), 4.64 (q, 1H), 3.59 (s, 3H), 3.25 (dd, 2H), 3.00-2.89 (m, 2H), 2.63-2.54 (m, 2H), 2.14-2.01 (m, 1H), 1.98-1.77 (m, 2H), 1.68-1.40 (m, 3H), 1.38 (d, 3H). Compound 1004: RT=12.7. $^1$H NMR (300 MHz, DMSO) δ 8.29 (d, J=7.3, 1H), 7.96-7.88 (m, 1H), 7.77 (d, 1H), 7.72 (d, 1H), 7.58-7.43 (m, 5H), 7.38 (d, 1H), 4.67 (q, 1H), 3.61 (s, 3H), 3.09-2.87 (m, 4H), 2.67-2.56 (m, 2H), 2.21-2.08 (m, 1H), 1.96-1.83 (m, 1H), 1.80-1.62 (m, 3H), 1.47-1.33 (m, 4H).

Example 2

3-{4-[(1R/S, 3R/S)-3-((R)-1-naphthalen-1-yl-ethylamino)-2-trifluoromethyl-phenyl}-propionic acid (compound 1005)

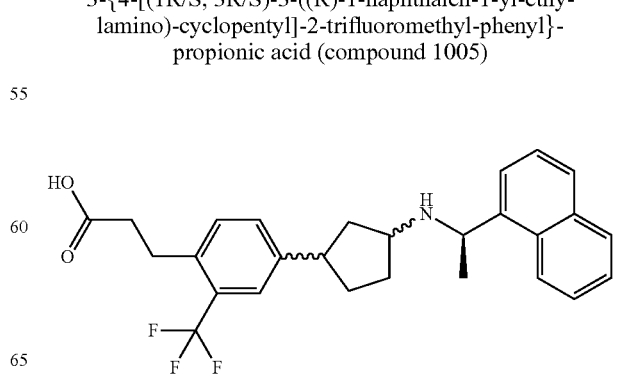

General procedure B was followed using 3-{4-[(1R/S, 3R/S)-3-((R)-1-naphthalen-1-yl-ethylamino)-cyclopentyl]-2-trifluoromethyl-phenyl}-propionic acid methyl ester (compound 1001). $^1$H NMR (300 MHz, DMSO) δ 8.36-8.25 (m, 1H), 8.03-7.87 (m, 3H), 7.65-7.47 (m, 5H), 7.43 (d, 1H), 5.20-5.02 (m, 1H), 3.36-3.21 (m, 1H), 2.96 (t, 3H), 2.52 (t, 2H), 2.26-2.12 (m, 1H), 2.02-1.73 (m, 5H), 1.61 (d, 3H).

Example 3:

3-{4-[(1R/S, 3R/S)-3-((R)-1-naphthalen-1-yl-ethylamino)-cyclopentyl]-2-trifluoromethyl-phenyl}-propionic acid (compound 1006)

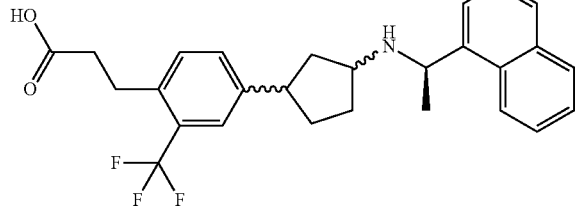

General procedure B was followed using 3-{4-[(1R/S,3R/S)-3-((R)-1-naphthalen-1-yl-ethylamino)-cyclopentyl]-2-trifluoromethyl-phenyl}-propionic acid methyl ester (compound 1002). $^1$H NMR (300 MHz, DMSO) δ 9.50 (br s, 1H), 8.35-8.25 (m, 1H), 7.97 (dd, 1H), 7.88 (t, , 2H), 7.64-7.50 (m, 3H), 7.46-7.34 (m, 3H), 5.15-4.93 (m, 1H), 3.47-3.27 (m, 2H), 2.93 (t, 2H), 2.50 (t, 2H), 2.35-2.18 (m, 1H), 2.15-1.99 (m, 2H), 1.77-1.39 (m, 6H).

Example 4

3-{4-[(1R/S,3R/S)-3-((R)-1-naphthalen-1-yl-ethylamino)-cyclopentyl]-2-trifluoromethyl-phenyl}-propionic acid (compound 1007)

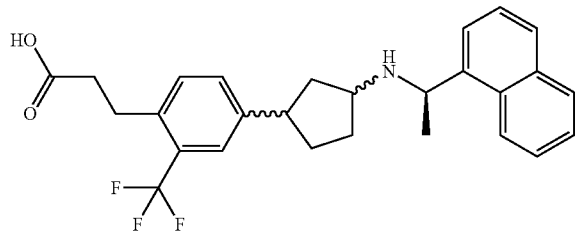 [SMILES: C[C@@H](NC1CCC(c2ccc(CCC(=O)O)c(C(F)(F)F)c2)C1)c1cccc2ccccc12]

General procedure B was followed using 3-{4-[(1R/S,3R/S)-3-((R)-1-naphthalen-1-yl-ethylamino)-cyclopentyl]-2-trifluoromethyl-phenyl}-propionic acid methyl ester (compound 1003). $^1$H NMR (300 MHz, DMSO) δ 8.31 (d, 1H), 8.00-7.92 (m, 1H), 7.85 (t, 2H), 7.62-7.49 (m, 3H), 7.45-7.34 (m, 3H), 4.99-4.85 (m, 1H), 3.34 (d, 2H), 2.93 (t, 2H), 2.55-2.44 (m, 2H), 2.14-1.88 (m, 3H), 1.83-1.65 (m, 2H), 1.58-1.38 (m, 4H).

Example 5

3-{4-[(1R/S,3R/S)-3-((R)-1-naphthalen-1-yl-ethylamino)-cyclopentyl]-2-trifluoromethyl-phenyl}-propionic acid (compound 1008)

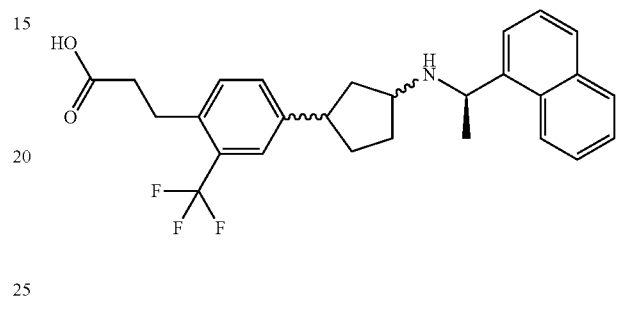

General procedure B was followed using 3-{4-[(1R/S,3R/S)-3-((R)-1-naphthalen-1-yl-ethylamino)-cyclopentyl]-2-trifluoromethyl-phenyl}-propionic acid methyl ester (compound 1004). $^1$H NMR (300 MHz, DMSO) δ 8.30 (d, 1H), 8.00-7.93 (m, 1H), 7.92-7.81 (m, 2H), 7.63-7.37 (m, 6H), 5.06-4.91 (m, 1H), 3.34-3.19 (m, 1H), 3.07-2.88 (m, 3H), 2.59-2.45 (m, 2H), 2.38-2.22 (m, 1H), 2.02-1.69 (m, 4H), 1.68-1.47 (m, 4H).

Preparation 4. 3-[4-((1S)-3-oxo-cyclopentyl)-2-trifluoromethyl-phenyl]-propionic acid methyl ester

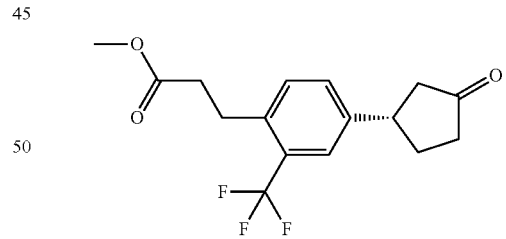

[Rh(S-BINAP)(nbd)]BF$_4$ (0.03 mmol) and 3-[4-(4,4,5,5-tetramethyl-[1,3,2]dioxaborolan-2-yl)-2-trifluoromethyl-phenyl]-propionic acid methyl ester (preparation 2) (1.5 mmol) were added to a 25 mL-flask containing a magnetic stirring bar and a septum inlet. The flask was flashed with argon. Triethylamine (1.5 mmol) and 2-cyclopenten-1-one (1.0 mmol) dissolved in aqueous 1,4-dioxane (6/1, 3 mL) were then added. The mixture was stirred for 6 h at 25° C.

Brine was added, the mixture was extracted with ethyl acetate, and the solvents were removed in vacuo to afford the title compound.

Example 6

3-(4-{(1S,3R)-3-[(R)-1-(4-fluoro-3-methoxy-phenyl)-ethylamino]-cyclopentyl}-2-trifluoromethyl-phenyl)-propionic acid methyl ester and 3-(4-{(1S,3S)-3-[(R)-1-(4-fluoro-3-methoxy-phenyl)-ethylamino]-cyclopentyl}-2-trifluoromethyl-phenyl)-propionic acid methyl ester (compounds 1009/1010)

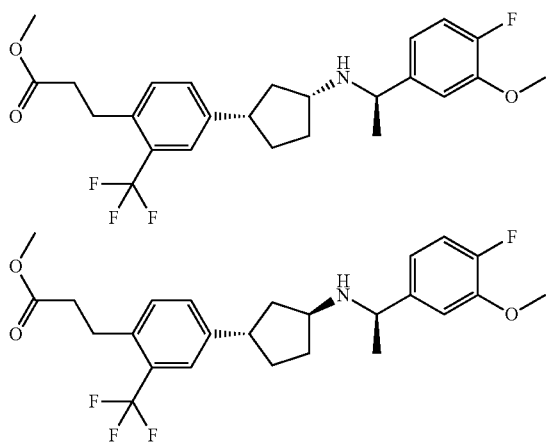

General procedure A was followed using 3-[4-((1S)-3-oxo-cyclopentyl)-2-trifluoromethyl-phenyl]-propionic acid methyl ester (preparation 4) as the ketone and (R)-1-(4-fluoro-3-methoxy-phenyl)-ethyl amine as the amine. The resulting 2 diastereomers (title compounds) were isolated by preparative chiral HPLC. Preparative chiral HPLC was performed on a Chiralpak AD-H column 250×20 mm at 25° C., UV detection at 280 nm. Isocratic separation with ethanol:n-heptan:NEt$_3$:CH$_3$COOH (10:90:0.1:0.1); flow rate=16 mL/min. Compound 1009: RT=9.52. Compound 1010: RT=12.03; $^1$H NMR (300 MHz, CDCl$_3$) δ 7.40 (s, 1H), 7.28-7.19 (m, 2H), 7.06-6.94 (m, 2H), 6.82 (ddd, 1H), 3.90 (s, 3H), 3.80 (q, 1H), 3.68 (s, 3H), 3.31-3.13 (m, 2H), 3.08 (t, 2H), 2.60 (dd, 2H), 2.22-2.06 (m, 2H), 1.88-1.65 (m, 2H), 1.62-1.31 (m, 3H), 1.35 (d, 3H).

Example 7

3-[4-[(1S,3R/S)-3-[[(1R)-1-(4-fluoro-3-methoxy-phenyl)ethyl]amino]cyclopentyl]-2-(trifluoromethyl)phenyl]propanoic acid (compound 1011)

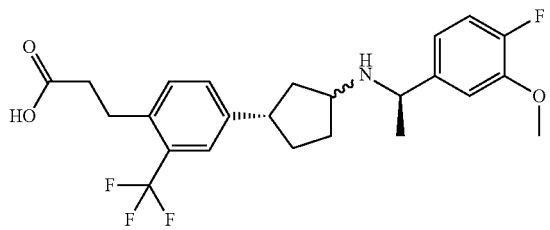 [SMILES: COc1cc([C@@H](C)NC2CC[C@H](c3ccc(CCC(=O)O)c(C(F)(F)F)c3)C2)ccc1F]

General procedure B was followed using 3-(4-{(1S,3R/S)-3-[(R)-1-(4-fluoro-3-methoxy-phenyl)-ethylamino]-cyclopentyl}-2-trifluoromethyl-phenyl)-propionic acid methyl ester (compound 1009). $^1$H NMR (300 MHz, DMSO) δ 7.55 (s, 1H), 7.49 (d, 1H), 7.40 (d, 1H), 7.20 (dd, 1H), 7.11 (dd, 1H), 6.91 (ddd, 1H), 3.83 (s, 3H), 3.82-3.73 (m, 1H), 3.05-2.87 (m, 4H), 2.56-2.44 (m, 2H), 2.29-2.16 (m, 1H), 1.97-1.84 (m, 1H), 1.81-1.33 (m, 4H), 1.27 (d, 3H).

Example 8

3-[4-[(1S,3R/S)-3-[[(1R)-1-(4-fluoro-3-methoxy-phenyl)ethyl]amino]cyclopentyl]-2-(trifluoromethyl)phenyl]propanoic acid (compound 1012)

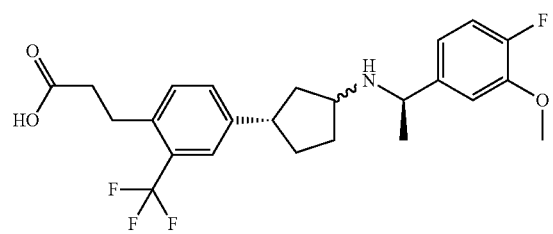 [SMILES: COc1cc([C@@H](C)NC2CC[C@H](c3ccc(CCC(=O)O)c(C(F)(F)F)c3)C2)ccc1F]

General procedure B was followed using 3-(4-{(1S,3R/S)-3-[(R)-1-(4-fluoro-3-methoxy-phenyl)-ethylamino]-cyclopentyl}-2-trifluoromethyl-phenyl)-propionic acid methyl ester (compound 1010). $^1$H NMR (300 MHz, DMSO) δ 9.91 (br s, 1H), 7.55-7.34 (m, 4H), 7.22 (dd, 1H), 7.13-7.02 (m, 1H), 4.30-4.11 (m, 1H), 3.86 (s, 3H), 3.46-3.22 (m, 2H), 2.94 (t, 2H), 2.50 (t, 2H), 2.18-2.00 (m, 3H), 1.91-1.67 (m, 2H), 1.63-1.39 (m, 4H).

Preparation 5. 2-[4-bromo-3-(trifluoromethyl)phenyl]-4,4,5,5-tetramethyl-1,3,2-dioxaborolane

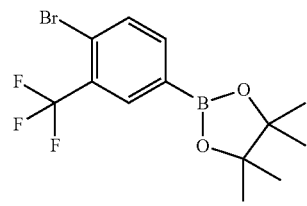 [SMILES: CC1(C)OB(c2ccc(Br)c(C(F)(F)F)c2)OC1(C)C]

A solution of 4-bromo-3-trifluoromethyl iodobenzene (McBee, E. T.; Pierce, O. R.; Lowery, R. D.; Rapkin, E.; J. Amer. Chem. Soc. (1951), 73, 3932-4) (51 g) in dry THF (500 mL) was cooled to −43° C., and isopropyl magnesiumchloride lithium chloride complex (230 mL, 1.3 M in THF) was added slowly. After 1 h at −43° C., the temperature was lowered to −70--60° C. and trimethylborate (24 mL) was added. The mixture was stirred another hour, keeping the temperature below −60° C., and then quenched with sat. NH$_4$Cl (aq., 200 mL). After 10 min, water (500 mL) and more sat. NH$_4$Cl (200 ml) were added, and the mixture was extracted with diethyl ether. The combined organic extracts were dried and concentrated to an oil. 2,3-Dimethyl-2,3-butanediol (17.2 g) was added, followed by toluene (200 mL), and the toluene was subsequently removed by evaporation. Additional toluene (200 mL) was added, followed by evaporation, leaving the title compound as a solid residue. The solid was crystallised from acetonitrile at 0° C. $^1$H NMR (300 MHz, DMSO) δ 7.98-7.90 (m, 2H), 7.82 (dd, J=8.0, 0.8, 1H), 1.31 (s, 12H).

Preparation 6. (R)-3-(4-bromo-3-trifluoromethyl-phenyl)-cyclopentanone

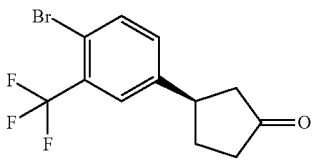 [SMILES: O=C1CC[C@@H](c2ccc(Br)c(C(F)(F)F)c2)C1]

2-[4-bromo-3-(trifluoromethyl)phenyl]-4,4,5,5-tetramethyl-1,3,2-dioxaborolane (3.0 g, 8.5 mmol) (Preparation 5) and [Rh(R-BINAP)(nbd)]BF$_4$ (155 mg) were dissolved in a de-gassed solution of 2-cyclopenten-1-one (0.70 g) in 1,4-dioxane (12.8 mL), water (2.5 mL), and triethylamine (1.2 mL) in a microwave vial and irradiated in a microwave reactor at 120° C. for 5 min. MTBE was added and the mixture was washed 3 times with water. The organic phase was dried, concentrated under reduced pressure and purified by flash chromatography (100% heptane->70% EtOAc/Heptane) to obtain the title compound. $^1$H NMR (300 MHz, CDCl$_3$) δ 7.68 (d, J=8.2, 1H), 7.57 (d, J=2.2, 1H), 7.28 (dd, J=8.4, 2.3, 1H), 3.51-3.36 (m, 1H), 2.76-2.64 (m, 1H), 2.56-2.23 (m, 4H), 2.06-1.89 (m, 1H).

Preparation 7. (R)-3-[4-(3-oxo-cyclopentyl)-2-trifluoromethyl-phenyl]-acrylic acid ethyl ester

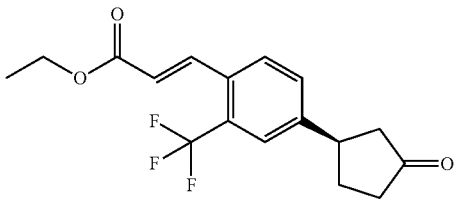 [SMILES: CCOC(=O)/C=C/c1ccc([C@@H]2CCC(=O)C2)cc1C(F)(F)F]

To a mixture of (R)-3-(4-bromo-3-trifluoromethyl-phenyl)-cyclopentanone (Preparation 6, 1.96 g), tri(o-tolyl)phosphine (120 mg), Pd(OAc)$_2$ (43 mg) and NaOAc (0.79 g) in DMF (13 mL) was added ethyl acrylate (0.79 g), and the reaction mixture was heated to 130° C. for 3 h. The mixture was diluted with EtOAc and washed with water. The organic phase was dried and concentrated in vacuo, and the residue was purified by flash chromatography using a gradient of heptane and EtOAc to obtain the title compound. $^1$H NMR (300 MHz, CDCl$_3$) δ 8.09-7.97 (m, 1H), 7.70 (d, 1H), 7.58 (d, 1H), 7.53-7.38 (m, 1H), 6.40 (d, 1H), 4.28 (q, 2H), 3.58-3.40 (m, 1H), 2.72 (dd, 1H), 2.58-2.26 (m, 4H), 2.10-1.92 (m, 1H), 1.34 (t, 3H).

Preparation 8. Ethyl 3-[4-[(1R)-3-oxocyclopentyl]-2-(trifluoromethyl)phenyl]propanoate

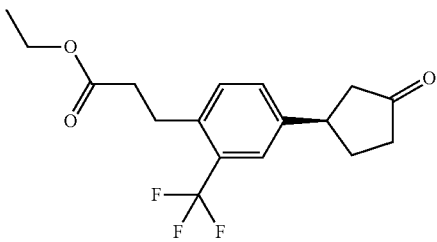 [SMILES: CCOC(=O)CCc1ccc([C@@H]2CCC(=O)C2)cc1C(F)(F)F]

A solution of (R)-3-[4-(3-oxo-cyclopentyl)-2-trifluoromethyl-phenyl]-acrylic acid ethyl ester (preparation 7, 1.55 g) in EtOAc (40 mL) containing Pd/C (300 mg) was hydrogenated overnight at rt. The catalyst was removed by filtration through Celite, and the filtrate was concentrated under reduced pressure, affording the title compound as a colorless oil. $^1$H NMR (300 MHz, CDCl$_3$) δ 7.54-7.48 (m, 1H), 7.39-7.24 (m, 2H), 4.14 (q, 2H), 3.51-3.35 (m, 1H), 3.12 (t, 2H), 2.75-2.23 (m, 7H), 2.05-1.90 (m, 1H), 1.25 (t, 3H).

Example 9

3-[4-[(1S,3S)-3-[[(1R)-1-(4-fluoro-2-methoxy-phenyl)ethyl]amino]cyclopentyl]-2-(trifluoromethyl)phenyl]propanoic acid and 3-[4-[(1S,3R)-3-[[(1R)-1-(4-fluoro-2-methoxy-phenyl)ethyl]amino]cyclopentyl]-2-(trifluoromethyl)phenyl]propanoic acid (compounds 1013/1014)

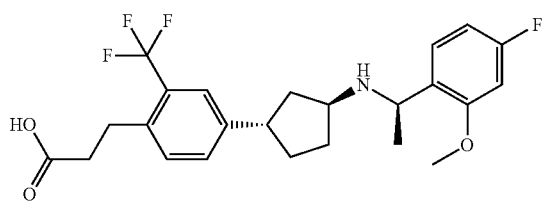

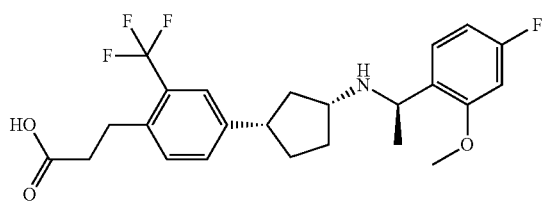

General procedure A was followed using Preparation 4 as the ketone and (R)-1-(4-fluoro-2-methoxyphenyl)-ethylamine as the amine. The intermediate methyl ester was hydrolyzed according to general procedure B. The two resulting diastereomers (title compounds) were isolated by preparative HPLC/MS and reanalyzed by analytical HPLC/MS. Compound 1013: RT=4.17; $^1$H NMR (600 MHz, DMSO) δ 7.45-7.35 (m, 4H), 6.84 (dd, 1H), 6.76-6.71 (m, 1H), 4.14-4.06 (m, 1H), 3.79 (s, 3H), 3.31-3.20 (m, 1H), 3.10-3.01 (m, 1H), 2.92 (t, 2H), 2.52-2.46 (m, 2H), 2.10-2.02 (m, 1H), 1.94-1.85 (m, 1H), 1.81-1.74 (m, 1H), 1.66-1.57 (m, 1H), 1.52-1.40 (m, 2H), 1.19 (d, 3H). Compound 1014: RT=4.27; $^1$H NMR (600 MHz, DMSO) δ 7.56 (d, 1H), 7.49 (d, 1H), 7.41 (dd, 1H), 6.84 (dd, 1H), 6.74 (td, 1H), 4.10 (q, 1H), 3.78 (s, 3H), 3.04-2.89 (m, 4H), 2.53-2.50 (m, 2H), 2.18-2.10 (m, 1H), 1.95-1.87 (m, 1H), 1.78-1.69 (m, 1H), 1.68-1.60 (m, 1H), 1.56-1.49 (m, 1H), 1.43-1.35 (m, 1H), 1.20 (d, 3H).

Example 10

Ethyl 3-[4-[(1R,3S)-3-[[(1R)-1-(4-fluoro-3-methoxy-phenyl)ethyl]amino]cyclopentyl]-2-(trifluoromethyl)phenyl]propanoate and ethyl 3-[4-[(1R,3R)-3-[[(1R)-1-(4-fluoro-3-methoxy-phenyl)ethyl]amino]cyclopentyl]-2-(trifluoromethyl)phenyl]propanoate (Compounds 1015/1016)

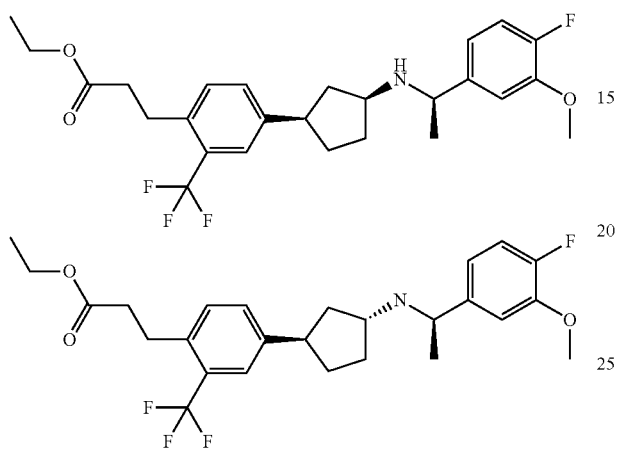

General procedure A was followed using ethyl 3-[4-[(1R)-3-oxocyclopentyl]-2-(trifluoromethyl)phenyl]propanoate (preparation 8) as the ketone and (R)-1-(4-fluoro-3-methoxyphenyl)-ethylamine as the amine. The two resulting diastereomers (title compounds) were isolated by preparative chiral HPLC. Preparative chiral HPLC was performed on a Chiralpak AD-H column (250×20 mm) at 25° C., UV detection at 280 nM. Isocratic separation with ethanol:n-heptane:NEt$_3$:CH$_3$COOH (10:90:0.1:0.1); flow rate=19 mL/min. Compound 1015: RT=11.2. $^1$H NMR (300 MHz, DMSO) δ 7.53 (s, 1H), 7.44 (dd, 2H), 7.18 (dd, 1H), 7.10 (dd, 1H), 6.93-6.86 (m, 1H), 4.08 (q, 2H), 3.78 (q, 1H), 3.04-2.88 (m, 1H), 2.65-2.56 (m, 2H), 2.16-2.03 (m, 1H), 2.00-1.56 (m, 4H), 1.42-1.27 (m, 1H), 1.25 (d, 3H), 1.17 (t, 3H). Compound 1016: RT=14.2. $^1$H NMR (300 MHz, DMSO) δ 7.48-7.35 (m, 3H), 7.20-7.05 (m, 2H), 6.93-6.85 (m, 1H), 4.08 (q, 2H), 3.75 (q, 1H), 3.36-3.21 (m, 1H), 3.06-2.93 (m, 3H), 2.65-2.55 (m, 2H), 2.13-1.29 (m, 6H), 1.25 (d, 3H), 1.17 (t, 3H).

Example 11

3-[4-[(1R,3R/S)-3-[[(1R)-1-(4-fluoro-3-methoxy-phenyl)ethyl]amino]cyclopentyl]-2-(trifluoromethyl)phenyl]propanoic acid (Compound 1017)

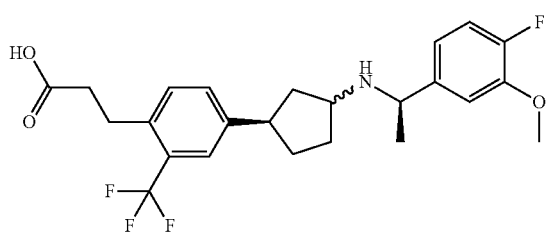 [SMILES: COc1cc([C@@H](C)NC2CC[C@@H](c3ccc(CCC(=O)O)c(C(F)(F)F)c3)C2)ccc1F]

General procedure B was followed using Compound 1015 as the ester. $^1$H NMR (300 MHz, DMSO) δ 7.57-7.36 (m, 3H), 7.19 (dd, 1H), 7.11 (dd, 1H), 6.95-6.86 (m, 1H), 3.83 (s, 3H), 3.87-3.74 (m, 1H), 3.04-2.87 (m, 4H), 2.54-2.43 (m, 2H), 2.16-2.04 (m, 1H), 1.99-1.58 (m, 4H), 1.45-1.31 (m, 1H), 1.27 (d, 3H).

Example 12

3-[4-[(1R,3R/S)-3-[[(1R)-1-(4-fluoro-3-methoxy-phenyl)ethyl]amino]cyclopentyl]-2-(trifluoromethyl)phenyl]propanoic acid (Compound 1018)

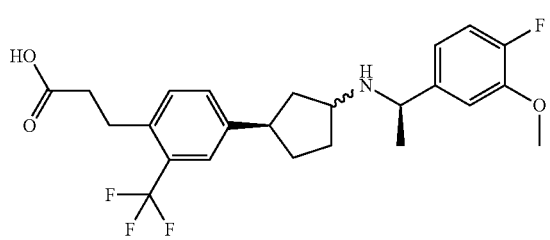 [SMILES: COc1cc([C@@H](C)NC2CC[C@@H](c3ccc(CCC(=O)O)c(C(F)(F)F)c3)C2)ccc1F]

General procedure B was followed using Compound 1016 as the ester. $^1$H NMR (300 MHz, DMSO) δ 7.46-7.35 (m, 3H), 7.16 (dd, J=8.6, 1.7, 1H), 7.10 (dd, J=11.5, 8.3, 1H), 6.93-6.84 (m, 1H), 3.82 (s, 3H), 3.77 (q, J=6.6, 1H), 3.33-3.19 (m, 1H), 2.95 (m, 3H), 2.53-2.42 (m, 2H), 2.10-1.81 (m, 3H), 1.66-1.30 (m, 3H), 1.25 (d, J=6.6, 3H).

Preparation 9. 4-(4,4,5,5-tetramethyl-[1,3,2]dioxaborolan-2-yl)-2-trifluoromethyl-phenol

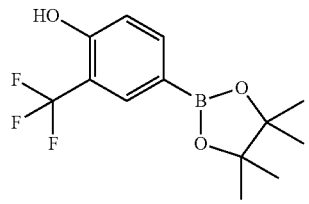 [SMILES: CC1(C)OB(c2ccc(O)c(C(F)(F)F)c2)OC1(C)C]

Pd$_2$(dba)$_3$ and PCy$_3$ were dissolved in 1,4-dioxane (35 mL) and stirred for 30 min. 4-bromo-1-trifluoromethylphenol (1.5 g, 6.21 mmol) was added followed by bis(pinacolato)diboron (1.73 g, 6.83 mmol) and potassium acetate (915 mg, 9.32 mmol). The reaction mixture was shaken at 80° C. for 5 h after which additional Pd$_2$(dba)$_3$ (85 mg) and PCy$_3$ (62 mg) were added. After 16 h at 80° C., the solvent was evaporated and the residue was purified by flash chromatography to obtain the title compound. $^1$H NMR (300 MHz, DMSO) δ 10.99 (s, 1H), 7.77-7.69 (m, 2H), 7.03 (d, 1H), 1.28 (s, 12H).

Preparation 10. (S)-3-(4-hydroxy-3-trifluoromethyl-phenyl)-cyclopentanone

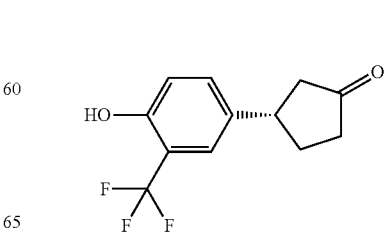

[Rh(S-BINAP)(nbd)]BF$_4$ (0.03 mmol) and 4-(4,4,5,5-tetramethyl-[1,3,2]dioxaborolan-2-yl)-2-trifluoromethyl-phenol (preparation 9) (1.5 mmol) were added to a 25 mL-flask containing a magnetic stir bar and a septum inlet. The flask was flushed with argon. Triethylamine (1.5 mmol) and 2-cyclopenten-1-one (1.0 mmol) dissolved in 1,4-dioxane—H$_2$O (6:1, 3 mL) were then added. The mixture was stirred for 6 h at 25° C. Brine was added, the mixture was extracted with ethyl acetate, and the solvents were removed in vacuo to afford the title compound. $^1$H NMR (300 MHz, DMSO) δ 10.37 (bs, 1H), 7.45-7.36 (m, 2H), 6.97 (d, 1H), 3.43-3.23 (m, 1H), 2.57-2.44 (m, 1H), 2.37-2.17 (m, 4H), 1.96-1.77 (m, 1H).

Example 13

4-[(1S)-3-[[(1R)-1-(4-fluoro-3-methoxy-phenyl)ethyl]amino]cyclopentyl]-2-(trifluoromethyl)phenol (Compound 1019, mixture of 2 diastereomers)

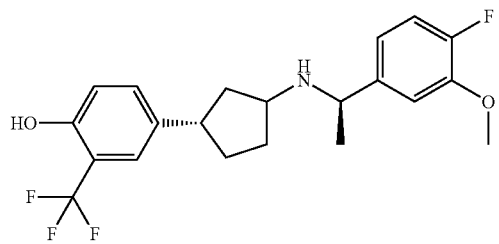 [SMILES: COc1cc([C@@H](C)NC2CC[C@H](c3ccc(O)c(C(F)(F)F)c3)C2)ccc1F]

General procedure A was followed using (S)-3-(4-hydroxy-3-trifluoromethyl-phenyl)-cyclopentanone (Preparation 10) as the ketone and (R)-1-(4-fluoro-3-methoxyphenyl)-ethylamine as the amine. $^1$H NMR (300 MHz, DMSO) δ 10.22 (bs, 1H), 7.39-7.20 (m, 2H), 7.19-7.04 (m, 2H), 6.96-6.84 (m, 2H), 3.82 (s, 3H), 3.73 (q, 1H), 3.26-2.79 (m, 2H), 2.24-1.27 (m, 7H), 1.23 (d, 3H).

Example 14

2-[4-[(1S)-3-[[(1R)-1-(4-fluoro-3-methoxy-phenyl)ethyl]amino]-cyclopentyl]-2-(trifluoromethyl)phenoxy]-2-methyl-propanoic acid (Compound 1020, mixture of 2 diastereomers)

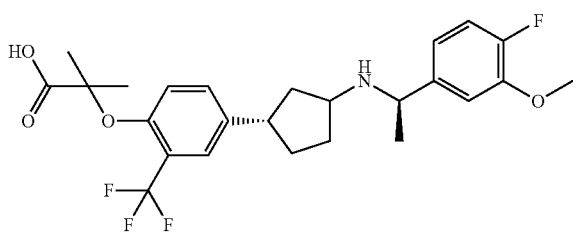 [SMILES: COc1cc([C@@H](C)NC2CC[C@H](c3ccc(OC(C)(C)C(=O)O)c(C(F)(F)F)c3)C2)ccc1F]

To compound 1019 (50 mg, 0.13 mmol) dissolved in acetonitrile (0.5 mL) was added ethyl 2-bromo-2-methylpropanoate (51 mg, 0.26 mmol) followed by K$_2$CO$_3$ (18 mg, 0.13 mmol). The reaction mixture was shaken at 80° C. for 22 h. Solids were filtered off, the solvent was removed under reduced pressure, and the residue was purified by preparative HPLC. The intermediate ester was hydrolyzed following general procedure B to afford the title compound as a mixture of 2 isomers. $^1$H NMR (300 MHz, DMSO) δ 7.69-7.58 (m, 1H), 7.55-7.31 (m, 2H), 7.31-7.20 (m, 1H), 7.20-7.10 (m, 1H), 6.92-6.81 (m, 1H), 4.41-4.27 (m, 1H), 3.87 (s, 3H), 3.28-3.09 (m, 1H), 3.03-2.84 (m, 1H), 2.39-1.72 (m, 6H), 1.60 (d, 3H), 1.51 (d, 6H).

Example 15

2-[4-[(1S)-3-[[(1R)-1-(4-fluoro-3-methoxy-phenyl)ethyl]amino]cyclopentyl]-2-(trifluoromethyl)phenoxy]acetic acid (Compound 1021, mixture of 2 diastereomers)

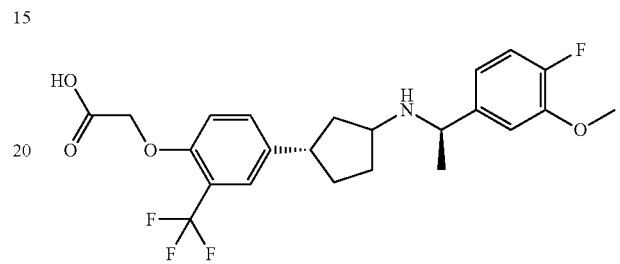

To compound 1019 (50 mg, 0.13 mmol) dissolved in acetonitrile (0.5 mL) was added ethyl bromoacetate (23 mg, 0.14 mmol) followed by K$_2$CO$_3$ (18 mg, 0.13 mmol). The reaction mixture was shaken at 50° C. for 5 h. Solids were filtered off, the solvent was removed under reduced pressure, and the residue was purified by preparative HPLC. The intermediate ester was hydrolyzed following general procedure B to afford the title compound as a mixture of isomers. $^1$H NMR (300 MHz, DMSO) δ 7.62-7.53 (m, 1H), 7.52-7.19 (m, 3H), 7.19-7.08 (m, 1H), 7.07-6.94 (m, 1H), 4.79-4.65 (m, 2H), 4.38-4.25 (m, 1H), 3.86 (s, 3H), 3.28-3.08 (m, 1H), 3.03-2.84 (m, 1H), 2.38-1.69 (m, 6H), 1.59 (s, 3H).

Preparation 10: [3-(4,4,5,5-Tetramethyl-[1,3,2]dioxaborolan-2-yl)-5-trifluoromethyl-phenoxy]-acetic acid ethyl ester

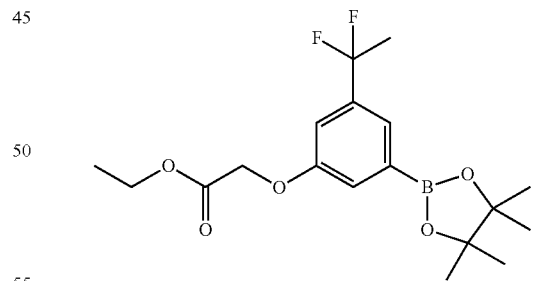

3-Borono-5-hydroxybenzotrifluoride (300 mg, 1.5 mmol) and 2,3-dimethyl-2,3-butandiol (173 mg, 1.5 mmol) were dissolved in THF (3 mL) and stirred for 5 min. Toluene (3 mL) was added and the solvent was evaporated. The addition of toluene followed by evaporation was repeated 3 times.

The crude boronic acid ester was dissolved in acetonitrile (3 mL) and treated with ethyl bromoacetate (2 eq.) and K$_2$CO$_3$ (2 eq.). The reaction mixture was stirred at rt for 3 days. Solids were filtered off, the solvent was removed under reduced pressure, and the residue was purified by chromatography affording the title compound. 1H NMR (300 MHz, DMSO) δ 7.49 (s, 1H), 7.38 (s, 2H), 4.94 (s, 2H), 4.18 (q, J=7.1 Hz, 2H), 1.30 (s, 12H), 1.20 (t, J=7.1 Hz, 3H).

Preparation 11: Ethyl 2-[3-[(1R)-3-oxocyclopentyl]-5-(trifluoromethyl)phenoxy]acetate

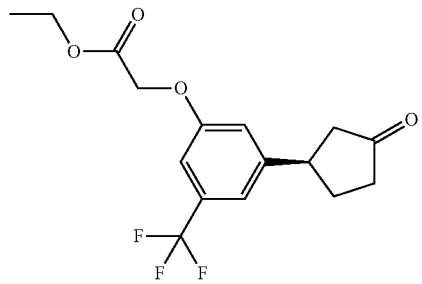 [SMILES: CCOC(=O)COc1cc([C@@H]2CCC(=O)C2)cc(C(F)(F)F)c1]

The title compound was prepared from [3-(4,4,5,5-Tetramethyl-[1,3,2]dioxaborolan-2-yl)-5-trifluoromethyl-phenoxy]-acetic acid ethyl ester and 2-cyclopenten-1-one with Rh(R-BINAP)(nbd)]BF$_4$ as catalyst in a manner similar to the one described for Preparation 6.

Example 16

2-[3-[(1R)-3-[[(1R)-1-(4-fluoro-3-methoxy-phenyl)ethyl]amino]-cyclopentyl]-5-(trifluoromethyl)phenoxy]acetic acid (compound 1022)

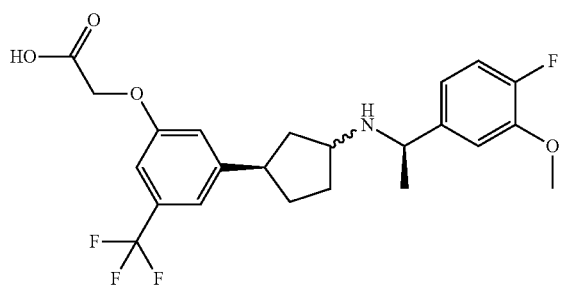 [SMILES: COc1cc([C@@H](C)NC2CC[C@@H](c3cc(OCC(=O)O)cc(C(F)(F)F)c3)C2)ccc1F]

General procedure A was followed using ethyl 2-[3-[(1R)-3-oxocyclopentyl]-5-(trifluoromethyl)phenoxy]acetate as the ketone and (R)-1-(4-fluoro-3-methoxyphenyl)-ethylamine hydrochloride as the amine. The resulting mixture of isomeric esters was purified and separated by flash chromatography (gradient of 0-80% EtOAc in heptane containing 2.5% NEt$_3$). The faster eluting peak was isolated and subjected to hydrolysis following general procedure B to afford the title compound. $^1$H NMR (300 MHz, DMSO) δ 7.40 (d, J=8.5 Hz, 1H), 7.17 (dd, J=11.4, 8.3 Hz, 1H), 7.11-6.97 (m, 3H), 6.94 (s, 1H), 4.46 (dd, 2H), 4.10 (q, 1H), 3.84 (s, 3H), 3.16-2.86 (m, 2H), 2.21-2.07 (m, 1H), 1.94-1.58 (m, 5H), 1.45 (d, J=6.6 Hz, 3H).

Example 17

{3-[(1R,3R/S)-3-((1R)-1-Naphthalen-1-yl-ethylamino)-cyclopentyl]-5-trifluoromethyl-phenoxy}-acetic acid (compound 1023)

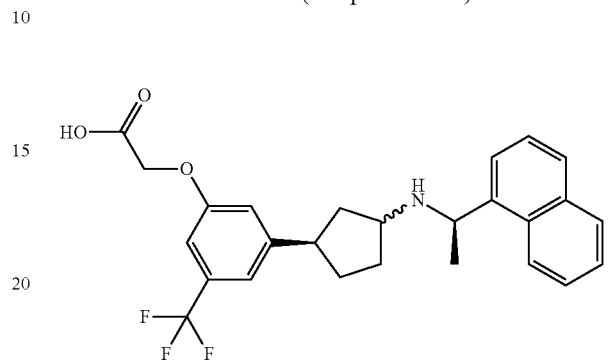

General procedure A was followed using ethyl 2-[3-[(1R)-3-oxocyclopentyl]-5-(trifluoromethyl)phenoxy]acetate as the ketone and (R)-1-naphthalen-1-yl-ethylamine as the amine. The resulting mixture of isomeric esters was purified and separated by flash chromatography (gradient of 0-80% EtOAc in heptane containing 2.5% NEt$_3$). The faster eluting peak was isolated and subjected to hydrolysis following general procedure B to afford the title compound. 1H NMR (300 MHz, DMSO) δ 8.26 (d, J=8.0 Hz, 1H), 7.98-7.91 (m, 1H), 7.83 (t, J=7.7 Hz, 2H), 7.60-7.47 (m, 3H), 7.10-7.03 (m, 2H), 6.94 (s, 1H), 4.90 (q, 1H), 4.51 (s, 2H), 3.21-3.07 (m, 1H), 3.00-2.83 (m, 1H), 2.29-2.15 (m, 1H), 1.93-1.51 (m, 5H), 1.49 (d, J=6.5 Hz, 3H).

Preparation 12:
4-Bromo-2-iodo-1-trifluoromethyl-benzene

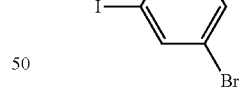

To a stirred solution of 5-bromo-2-(trifluoromethyl)aniline (300 mg, 1.255 mM) in dry THF (10 mL) was added BF$_3$-etherate (707 mg, 5.02 mM) and tert-butyl nitrite (452 mg, 4.39 mM) at −78° C. Reaction mixture was stirred for 10 min, warmed to room temperature and maintained for 30 min. The reaction mixture was diluted with diethyl ether (30 mL). The solid was filtered off and dried under vacuum. This diazonium salt was added to a mixture of KI (289 mg, 1.746 mM) and iodine (203 mg, 0.876 mM) in acetone taken in an another flask at 0° C. and stirred at room temperature for 1 h. After completion of the reaction, the reaction mixture was concentrated under reduced pressure. The obtained residue was diluted with water (20 mL) and the product was extracted with diethyl ether (2×20 mL). The combined organic layer was dried over anhydrous sodium sulphate and concentrated under reduced pressure to afford the title compound as a liquid (230 mg, 68%). 1H NMR (400 MHz, CDCl$_3$) δ 8.19 (s, 1H), 7.59 (d, 1H), 7.50 (d, 1H).

Preparation 13:
3-(5-Bromo-2-trifluoromethyl-phenyl)-acrylic acid methyl ester

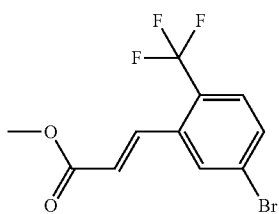 [SMILES: COC(=O)/C=C/c1cc(Br)ccc1C(F)(F)F]

To a stirred solution of triphenylphosphine (486 mg, 1.857 mM) and Palladium acetate (159.9 mg, 0.714 mM) in dry THF taken in a sealed tube was added triethylamine (0.4 mL, 2.857 mM) at room temperature. Reaction mixture was degassed for 10 min, and then stirred for 15 min. To this 4-Bromo-2-iodo-1-(trifluoromethyl)benzene, methylacrylate (157 mg, 1.57 mM) were added followed by the addition of potassium carbonate (394 mg, 2.887 mM) at RT. Reaction mixture was heated to 80° C. for 16 h. After completion of reaction, reaction mixture was cooled to room temperature and passed through celite bed, washed with ethyl acetate. The filtrate was concentrated under reduced pressure. The crude product was purified by column chromatography (silica gel, 0-5% ethyl acetate in pet ether) to afford the title compound as a solid (200 mg, 76%). 1H NMR (400 MHz, CDCl$_3$) δ 7.96 (d, 1H), 7.82 (s, 1H), 7.62 (d, 1H), 7.56 (d, 1H), 6.40 (d, 1H), 3.80 (s, 3H).

Preparation 14: 3-[5-(4,4,5,5-Tetramethyl-[1,3,2] dioxaborolan-2-yl)-2-trifluoromethyl-phenyl]-acrylic acid methyl ester

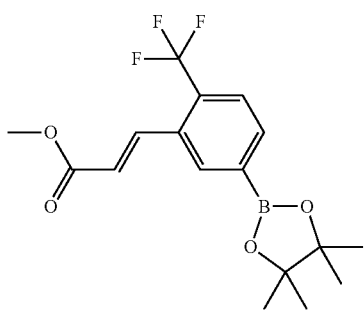

To a stirred solution of (E)-methyl 3-(5-bromo-2-(trifluoromethyl)phenyl)acrylate (400 mg, 1.298 mM) in 1,4-dioxane was added PdCl$_2$(PPh$_3$)$_2$. Reaction mixture was degassed with argon for 10 min and then heated to 55-60° C. To this Bispinacalato diboran (657 mg, 2.597 mM), potassium acetate (254 mg, 2.597 mM) and triethyl amine (0.3 mL, 2.597 mM) were added. The reaction mixture was heated to 90-100° C. for 3 h. Reaction mixture was cooled to room temperature and diluted with ethyl acetate (20 mL). Reaction mixture was passed through celite, washed with ethyl acetate (20 mL). Filtrate was concentrated under reduced pressure to afford the title compound as a liquid. The crude product was directly taken for the next without purification (Crude yield: 510 mg, 60%). 1H NMR (400 MHz, CDCl$_3$) δ 8.18-8.00 (m, 2H), 7.88 (m, 1H), 7.69 (m, 1H), 6.50 (d, 1H), 3.81 (s, 3H), 1.23 (s, 12H).

Preparation 15: Methyl 3-(5-(4,4,5,5-tetramethyl-1,3,2-dioxaborolan-2-yl)-2-(trifluoromethyl)phenyl propanoate

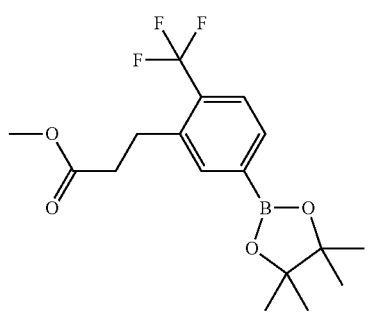

To a stirred solution of (E)-Methyl 3-(5-(4,4,5,5-tetramethyl-1,3,2-dioxaborolan-2-yl)-2-(trifluoromethyl)phenyl) acrylate (500 mg, 1.404 mM) in methanol (10 mL) was added 10% Palladium carbon (500 mg). Reaction mixture was stirred under hydrogen atmosphere (balloon pressure) at RT for 30 h. Reaction mixture was filtered through celite bed and washed with methanol (10 mL). Filtrate was concentrated under reduced pressure to afford title compound as a liquid (490 mg, 86%). 1H NMR (400 MHz, CDCl$_3$) δ 7.78-7.70 (m, 2H), 7.61 (d, 1H), 3.69 (s, 3H), 3.18-3.08 (m, 2H), 2.69-2.58 (m, 2H), 1.24 (s, 12H).

Preparation 16: 3-[5-((1R)-3-oxo-cyclopentyl)-2-trifluoromethyl-phenyl]-propionic acid methyl ester

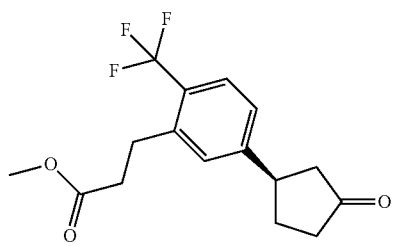 [SMILES: COC(=O)CCc1cc([C@@H]2CCC(=O)C2)ccc1C(F)(F)F]

The title compound was prepared from Methyl 3-(5-(4,4,5,5-tetramethyl-1,3,2-dioxaborolan-2-yl)-2-(trifluoromethyl)phenyl propanoate (preparation 15) and 2-cyclopenten- 1-one with Rh(R-BINAP)(nbd)]BF$_4$ as catalyst in a manner similar to the one described for Preparation 6.

Example 18

3-[5-[(1R)-3-[[(1R)-1-(1-naphthyl)ethyl]amino]cyclopentyl]-2-(trifluoromethyl)phenyl]propanoic acid (mixture of 2 stereoisomers) (compound 1024)

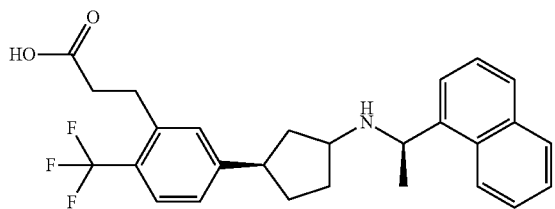 [SMILES: C[C@@H](NC1CC[C@@H](c2ccc(C(F)(F)F)c(CCC(=O)O)c2)C1)c1cccc2ccccc12]

General procedure A was followed using 3-[5-((1R)-3-oxo-cyclopentyl)-2-trifluoromethyl-phenyl]-propionic acid methyl ester (preparation 16) as the ketone and (R)-1-naphthalen-1-yl-ethylamine as the amine. The resulting mixture of isomeric esters was purified and separated by flash chromatography. The faster eluting peak was isolated and subjected to hydrolysis following general procedure B to afford the title compound. 1H NMR (600 MHz, DMSO) δ 8.30 (d, J=8.2 Hz, 1H), 7.93 (d, J=8.0 Hz, 1H), 7.84-7.75 (m, 2H), 7.59-7.48 (m, 4H), 7.41-7.17 (m, 2H), 4.78 (s, 1H), 3.35-3.06 (m, 2H), 2.99-2.88 (m, 2H), 2.55-2.42 (m, 2H), 2.24-1.67 (m, 4H), 1.63-1.39 (m, 5H).

The invention claimed is:
1. A compound according to formula I

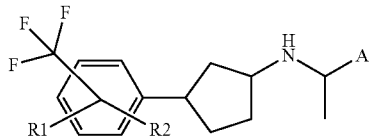

wherein
A represents $C_{6-10}$aryl, $C_{1-9}$heterocycloalkylphenyl, $C_{1-9}$heteroaryl or $C_{3-7}$cycloalkyl, wherein said $C_{6-10}$aryl, $C_{1-9}$heterocycloalkylphenyl, $C_{1-9}$heteroaryl or $C_{3-7}$cycloalkyl is optionally further substituted with one or more, same or different substituents represented by halogen, hydroxy, mercapto, trifluoromethyl, cyano, carboxy, —C(O)H, —NH$_2$, —C(O)NH$_2$, nitro, oxo, —S(O)$_2$NH$_2$, $C_{1-6}$alkyl, $C_{2-4}$alkenyl, $C_{2-4}$alkynyl, $C_{1-6}$hydroxyalkyl, $C_{1-6}$haloalkyl, $C_{1-6}$alkoxy, $C_{1-4}$alkoxycarbonyl, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-7}$cycloalkyl, $C_{3-7}$cycloalkenyl, $C_{1-6}$amino, iminomethyl, $C_{1-4}$aminosulfonyl, $C_{1-4}$aminocarbonyloxy, $C_{1-4}$alkylsulfonylamino, hydroxyiminomethyl, $C_{1-4}$alkylcarbonylamino, $C_{1-4}$alkylsulfonyl, $C_{1-6}$ heterocycloalkyl, $C_{2-6}$heterocycloalkenyl, $C_{1-5}$heteroaryl or phenyl;
R$_1$ represents one or more, same or different substituents selected from halogen, cyano, —NH$_2$, carboxy, $C_{1-6}$-amino, hydroxy, mercapto, —C(O)H, —C(O)NH$_2$, nitro, oxo, hydroxymethyl, $C_{1-6}$alkoxy, carboxy$C_{1-4}$ alkoxy, $C_{1-6}$alkoxycarbonyl, $C_{1-6}$alkoxycarbonyl$C_{1-6}$ alkoxy, carboxy$C_{1-4}$alkyl, $C_{1-6}$alkoxycarbonyl$C_{1-4}$ alkyl, $C_{1-6}$alkylcarbonyl, $C_{1-6}$aminocarbonyl, hydroxyaminocarbonyl, $C_{3-6}$cycloalkylaminocarbonyl, $C_{1-6}$heterocycloalkylaminocarbonyl, $C_{3-6}$cycloalkylamino, $C_{1-6}$ heterocycloalkylcarbonyl, $C_{6-14}$aryl, $C_{1-9}$heteroaryl, $C_{1-6}$heteroarylaminocarbonyl, —S(O)$_2$NH$_2$, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-6}$heterocycloalkyloxy, $C_{1-6}$alkylthio, $C_{1-6}$aminosulfonyl, $C_{1-6}$aminocarbonyloxy, $C_{1-6}$alkylsulfonylamino, $C_{1-6}$alkylsulfonylamino$C_{1-3}$ alkyl, $C_{6-10}$ arylamino, $C_{6-10}$arylaminocarbonyl, $C_{6-10}$aryloxycarbonyl, $C_{1-4}$alkoxycarbamoyl, $C_{6-10}$arylcarbonylamino, $C_{6-10}$arylsulfonylamino, $C_{1-6}$alkylcarbonylamino, $C_{1-3}$ alkylcarbonylaminoalkyl, $C_{2-6}$alkenylcarbonylamino, $C_{3-6}$cycloalkenylcarbonylamino, $C_{3-6}$ cycloalkylcarbonylamino, $C_{1-4}$alkoxycarbonylamino, $C_{1-6}$heterocycloalkylcarbonylamino, $C_{1-6}$alkylsulfonyl, $C_{1-6}$hetero cycloalkylsulfonyl or $C_{1-4}$ alkylsulfonylamino carbonyl, iminomethyl, hydroxyiminomethyl, amidino, trifluoromethyl, $C_{1-6}$alkyl, $C_{2-4}$alkenyl, $C_{2-6}$alkynyl, $C_{1-6}$hydroxyalkyl, amino$C_{1-6}$alkyl, $C_{1-6}$ haloalkyl, $C_{3-7}$ cycloalkyl, $C_{3-7}$cycloalkenyl, $C_{1-6}$ heterocycloalkyl, $C_{2-6}$heterocycloalkenyl, methoxycarbonyl$C_{1-3}$ alkyl or carboxy$C_{6-10}$aryl, wherein said $C_{1-6}$amino, $C_{1-6}$alkoxy, carboxy$C_{1-4}$alkoxy, $C_{1-6}$alkoxycarbonyl, $C_{1-6}$alkylcarbonyl, $C_{1-6}$aminocarbonyl, $C_{3-6}$cycloalkylaminocarbonyl, $C_{1-6}$ heterocycloalkylaminocarbonyl, $C_{3-6}$cycloalkylamino, $C_{1-6}$ heterocycloalkylcarbonyl, $C_{6-14}$aryl, $C_{1-9}$heteroaryl, $C_{1-6}$heteroarylaminocarbonyl, $C_{1-6}$ureido, $C_{1-6}$thioureido, $C_{1-4}$alkylcarbonyloxy, $C_{1-4}$alkoxycarbonyloxy, $C_{1-4}$alkoxysulfonyloxy, $C_{1-6}$heterocycloalkyloxy, $C_{1-6}$ alkylthio, $C_{1-6}$aminosulfonyl, $C_{1-6}$aminocarbonyloxy, $C_{1-6}$alkylsulfonylamino, $C_{1-6}$ alkylsulfonylamino $C_{1-3}$alkyl, $C_{6-10}$arylamino, $C_{6-10}$arylaminocarbonyl, $C_{6-10}$aryloxycarbonyl, $C_{1-4}$alkoxycarbamoyl, $C_{6-10}$ arylcarbonylamino, $C_{6-10}$arylsulfonylamino, $C_{1-6}$alkylcarbonylamino, $C_{2-6}$alkenylcarbonylamino, $C_{3-6}$cycloalkenylcarbonylamino, $C_{3-6}$cycloalkylcarbonylamino, $C_{1-6}$alkoxycarbonylamino, $C_{1-6}$heterocycloalkylcarbonylamino, $C_{1-6}$alkylsulfonyl, $C_{1-6}$heterocycloalkylsulfonyl or $C_{1-4}$alkylsulfonylaminocarbonyl, $C_{1-6}$alkyl, $C_{2-6}$alkenyl, $C_{2-6}$alkynyl, $C_{1-6}$hydroxyalkyl, amino$C_{1-6}$alkyl, $C_{1-6}$haloalkyl, $C_{3-7}$cycloalkyl, $C_{3-7}$cycloalkenyl, $C_{1-6}$heterocycloalkyl, $C_{2-6}$heterocycloalkenyl, or carboxy$C_{6-10}$aryl are optionally substituted with one or more, same or different substituents selected from the group consisting of halogen, trifluoromethyl, hydroxy, cyano or $C_{1-4}$alkyl;
R$_2$ represents one or more, same or different substituents selected from hydrogen, cyano, halogen, carboxy, —C(O)NH$_2$, $C_{1-4}$alkyl, $C_{2-4}$alkenyl, $C_{2-4}$alkynyl, $C_{1-6}$hydroxyalkyl, $C_{1-6}$haloalkyl, amino$C_{1-6}$alkyl, $C_{3-6}$cycloalkyl, $C_{1-6}$heterocycloalkyl, $C_{1-6}$alkoxy, $C_{1-6}$aminocarbonyl, $C_{6-10}$aryloxycarbonyl, $C_{1-6}$amino, $C_{6-10}$ arylamino, $C_{1-4}$ alkoxycarbonylamino, $C_{1-4}$ alkylcarbonylamino, $C_{2-4}$ alkenylcarbonylamino, $C_{3-6}$ cycloalkylcarbonylamino or $C_{1-6}$ heterocycloalkylcarbonylamino,
or pharmaceutically acceptable stereoisomers, salts or in vivo hydrolysable esters thereof.

2. A compound according to claim 1, of formula Ia

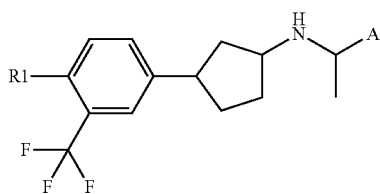

3. A compound according to claim 1, of formula Ib,

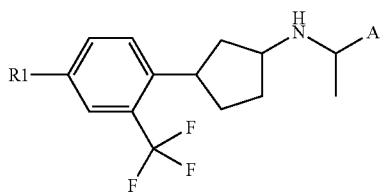

4. A compound according to claim 1, wherein R$_2$ represents hydrogen.

5. A compound according to any one of claims 1-4, wherein R$_1$ represents halogen, cyano, —NH$_2$, carboxy, hydroxy, —C(O)H, oxo, hydroxymethyl, C$_{1-4}$alkoxy, C$_{1-4}$amino, mercapto, —C(O)NH$_2$, nitro, carboxyC$_{1-4}$alkoxy, C$_{1-4}$alkoxycarbonyl, C$_{1-4}$alkoxycarbonylC$_{1-4}$alkoxy, carboxyC$_{1-4}$alkyl, C$_{1-4}$alkoxycarbonylC$_{1-4}$alkyl, C$_{1-4}$alkylcarbonyl, C$_{1-4}$aminocarbonyl, hydroxyaminocarbonyl, C$_{3-6}$ cycloalkylaminocarbonyl, C$_{1-5}$heterocycloalkylaminocarbonyl, C$_{3-6}$ cycloalkylamino, C$_{1-5}$heterocycloalkylcarbonyl, C$_{6-10}$ aryl, C$_{3-9}$heteroaryl, C$_{1-5}$heteroarylaminocarbonyl, —S(O)$_2$NH$_2$, C$_{1-4}$ureido, C$_{1-4}$thioureido, C$_{1-4}$ alkylcarbonyloxy, C$_{1-4}$alkoxycarbonyloxy, C$_{1-4}$alkoxysulfonyloxy, C$_{1-5}$heterocycloalkyloxy, C$_{1-4}$alkylthio, C$_{1-4}$aminosulfonyl, C$_{1-4}$aminocarbonyloxy, C$_{1-4}$ alkylsulfonylamino, C$_{1-4}$alkylsulfonylaminoC$_{1-3}$alkyl, C$_{6-10}$arylamino, C$_{6-10}$arylaminocarbonyl, C$_{6-10}$aryloxycarbonyl, C$_{1-3}$alkoxycarbamoyl, C$_{6-10}$arylcarbonylamino, C$_{6-10}$arylsulfonylamino, C$_{1-4}$alkylcarbonylamino, C$_{1-3}$alkylcarbonylaminomethyl, C$_{2-4}$alkenylcarbonylamino, C$_{3-6}$cycloalkenylcarbonylamino, C$_{3-6}$cycloalkylcarbonylamino, C$_{1-4}$alkoxycarbonylamino, C$_{1-5}$heterocycloalkylcarbonylamino, C$_{1-4}$ alkylsulfonyl, C$_{1-5}$heterocycloalkylsulfonyl or C$_{1-4}$alkylsulfonylaminocarbonyl, iminomethyl, hydroxyiminomethyl, amidino, trifluoromethyl, C$_{1-5}$alkyl, C$_{2-4}$alkenyl, C$_{2-4}$alkynyl, C$_{1-4}$hydroxyalkyl, aminoC$_{1-4}$alkyl, C$_{1-4}$haloalkyl, C$_{3-6}$cycloalkyl, C$_{3-6}$cycloalkenyl, C$_{1-5}$heterocycloalkyl or C$_{2-5}$heterocycloalkenyl.

6. A compound according to claim 1, wherein R$_1$ represents hydroxy, C$_{1-4}$alkyl or C$_{1-4}$alkoxy, wherein said C$_{1-4}$alkyl or C$_{1-4}$alkoxy is optionally substituted with carboxy or C$_{1-4}$alkoxycarbonyl.

7. A compound according to claim 6, wherein R$_1$ represents carboxyethyl, hydroxy, carboxymethoxy, carboxylsopropoxy, methoxycarbonylethyl, or ethoxycarbonylethyl.

8. A compound according to claim 1, wherein A represents C$_{6-10}$aryl optionally further substituted with one or more, same or different substituents represented by halogen, hydroxy, trifluoromethyl, cyano, carboxy, —C(O)H, —NH$_2$, —C(O)NH$_2$, C$_{1-6}$alkyl, C$_{2-6}$alkenyl, C$_{2-6}$alkynyl, C$_{1-6}$hydroxyalkyl, C$_{1-6}$haloalkyl, C$_{1-4}$alkoxy or phenyl.

9. A compound according to claim 8, wherein A represents naphthyl or phenyl, wherein said naphthyl or phenyl is optionally substituted with one or more, same or different substituents represented by halogen, hydroxy, trifluoromethyl, cyano, carboxy, —NH$_2$, C$_{1-6}$alkyl, C$_{1-6}$hydroxyalkyl, C$_{1-6}$haloalkyl or C$_{1-4}$alkoxy.

10. A compound according to claim 9, wherein A represents naphthyl, 4-fluoro-3-methoxy-phenyl or 4-fluoro-2-methoxy-phenyl.

11. A compound according to claim 1 selected from the group consisting of:
- 3-{4-[(1R, 3R)-3-((R)-1-naphthalen-1-yl-ethylamino)-cyclopentyl]-2-trifluoromethyl-phenyl}-propionic acid methyl ester,
- 3-{4-[(1R, 3S)-3-((R)-1-naphthalen-1-yl-ethylamino)-cyclopentyl]-2-trifluoromethyl-phenyl}-propionic acid methyl ester,
- 3-{4-[(1S, 3S)-3-((R)-1-naphthalen-1-yl-ethylamino)-cyclopentyl]-2-trifluoromethyl-phenyl}-propionic acid methyl ester,
- 3-{4-[(1S, 3R)-3 ((R)-1-naphthalen-1-yl-ethylamino)-cyclopentyl]-2-trifluoromethyl-phenyl}-propionic acid methyl ester,
- 3-{4-[(1R, 3R)-3-((R)-1-naphthalen-1-yl-ethylamino)-cyclopentyl]-2-trifluoromethyl-phenyl}-propionic acid,
- 3-{4-[(1R, 3S)-3-((R)-1-naphthalen-1-yl-ethylamino)-cyclopentyl]-2-trifluoromethyl-phenyl}-propionic acid,
- 3-{-4-[(1S, 3S)-3-((R)-1-naphthalen-1-yl-ethylamino)-cyclopentyl]-2-trifluoromethyl-phenyl}-propionic acid,
- 3-{4-[(1S, 3R)-3-((R)-1-naphthalen-1-yl-ethylamino)-cyclopentyl]-2-trifluoromethyl-phenyl}-propionic acid,
- 3-(4-{(1S, 3R)-3-[(R)-1-(4-fluoro-3-methoxy-phenyl)-ethylamino]-cyclopentyl}-2-trifluoromethyl-phenyl)-propionic acid methyl ester,
- 3-(4-{(1S, 3S)-3-[(R)-1-(4-fluoro-3-methoxy-phenyl)-ethylamino]-cyclopentyl}-2-trifluoromethyl-phenyl)-propionic acid methyl ester,
- 3-[4-[(1S, 3R)-3-[[(1R)-1-(4-fluoro-3-methoxy-phenyl)ethyl]amino]cyclopentyl]-2-(trifluoromethyl)phenyl]propionic acid,
- 3-[4-[(1S, 3S)-3-[[(1R)-1-(4-fluoro-3-methoxy-phenyl)ethyl]amino]cyclopentyl]-2-(trifluoromethyl)phenyl]propanoic acid,
- 3-[4-[(1S, 3S)-3-[[(1R)-1-(4-fluoro-2-methoxy-phenyl)ethyl]amino]cyclopentyl]-2-(trifluoromethyl)phenyl]propanoic acid,
- 3-[4-[(1S, 3R)-3-[[(1R)-1-(4-fluoro-2-methoxy-phenyl)ethyl]amino]cyclopentyl]-2-(trifluoromethyl)phenyl]propanoic acid,
- ethyl 3-[4-[(1R, 3R)-3-[[(1R)-1-(4-fluoro-3-methoxyphenyl)ethyl]amino]cyclopentyl]-2-(trifluoromethyl)phenyl]propanoate,
- ethyl 3-[4-[(1R, 3S)-3-[[(1R)-1-(4-fluoro-3-methoxy-phenyl)ethyl]amino]cyclopentyl]-2-(trifluoromethyl)phenyl]propanoate,
- 3-[4-[(1R, 3S)-3-[[(1R)-1-(4-fluoro-3-methoxy-phenyl)ethyl]amino]cyclopentyl]-2-(trifluoromethyl)phenyl]propanoic acid,
- 3-[4-[(1R, 3R)-3-[[(1R)-1-(4-fluoro-3-methoxy-phenyl)ethyl]amino]cyclopentyl]-2-(trifluoromethyl)phenyl]propanoic acid,
- 4-[(1S)-3-[[(1R)-1-(4-fluoro-3-methoxy-phenyl)ethyl]amino]cyclopentyl]-2-(trifluoromethyl)phenol (mixture of two diastereomers), 2-[4-[(1S)-3-[[(1R)-1-(4-fluoro-3-methoxy-phenyl)ethyl]amino]cyclopentyl]-2-(trifluoromethyl)phenoxy]-2-methyl-propanoic acid (mixture of two diastereomers), and 2-[4-[(1S)-3-[[(1R)-1-(4-fluoro-3-methoxy-phenyl)ethyl]amino]cyclopentyl]-2-(trifluoromethyl)phenoxy]acetic acid (mixture of two diastereomers).

12. A compound according to claim 1 selected from the group consisting of:

2-[3-[(1R)-3-[[(1R)-1-(4-fluoro-3-methoxy-phenyl)ethyl]amino]-cyclopentyl]-5-(trifluoromethyl)phenoxy]acetic acid, {3-[(1R,3R/S)-3-((1R)-1-Naphthalen-1-yl-ethylamino)-cyclopentyl]-5-trifluoromethyl-phenoxy}-acetic acid, and 3-[5-[(1R)-3-[[(1R)-1-(1-naphthyl)ethyl]amino]cyclopentyl]-2-(trifluoromethyl)phenyl]propanoic acid.

13. An intermediate for the preparation of compounds according to claim 1 selected from the group consisting of:

3-[4-(4,4,5,5-tetramethyl-[1,3,2]dioxaborolan-2-yl)-2-trifluoromethyl-phenyl]-acrylic acid methyl ester, 3-[4-(4,4,5,5-tetramethyl-[1,3,2]dioxaborolan-2-yl)-2-trifluoromethyl-phenyl]-propionic acid methyl ester, rac-3-[4-(3-oxo-cyclopentyl)-2-trifluoromethyl-phenyl]-propionic acid methyl ester, 3-[4-((1S)-3-oxo-cyclopentyl)-2-trifluoromethyl-phenyl]-propionic acid methyl ester, 2-[4-bromo-3-(trifluoromethyl)phenyl]-4,4,5,5-tetramethyl-1,3,2-dioxaborolane, (R)-3-(4-bromo-3-trifluoromethyl-phenyl)-cyclopentanone, (R)-3-[4-(3-oxo-cyclopentyl)-2-trifluoromethyl-phenyl]-acrylic acid ethyl ester, ethyl 3-[4-[(1R)-3-oxocyclopentyl]-2-(trifluoromethyl)phenyl]propanoate, 4-(4,4,5,5-tetramethyl-[1,3,2]dioxaborolan-2-yl)-2-trifluoromethyl-phenol, or (S)-3-(4-hydroxy-3-trifluoromethyl-phenyl)-cyclopentanone, Ethyl 2-[3-[(1R)-3-oxocyclopentyl]-5-(trifluoromethyl)phenoxy]acetate, 4-Bromo-2-iodo-1-trifluoromethyl-benzene, 3-(5-Bromo-2-trifluoromethyl-phenyl)-acrylic acid methyl ester, 3-[5-(4,4,5,5-Tetramethyl-[1,3,2]dioxaborolan-2-yl)-2-trifluoromethyl-phenyl]-acrylic acid methyl ester, Methyl 3-(5-(4,4,5,5-tetramethyl-1,3,2-dioxaborolan-2-yl)-2-(trifluoromethyl)phenyl propanoate, and 3-[5-((1R)-3-Oxo-cyclopentyl)-2-trifluoromethyl-phenyl]-propionic acid methyl ester.

14. A method of treating or ameliorating hyperparathyroidism the method comprising administering to a patient in need thereof an effective amount of a compound according to claim 1.

15. A pharmaceutical composition comprising a compound according to claim 1 or a pharmaceutically acceptable stereoisomer, salt or in vivo hydrolysable ester thereof, together with a pharmaceutically acceptable vehicle or excipient.

16. A method of treating or ameliorating parathyroid carcinoma, parathyroid adenoma, primary parathyroid hyperplasia, chronic renal failure, chronic kidney disease, polycystic kidney disorder, podocyte-related diseases, primary hyperparathyroidism, secondary hyperparathyroidism, tertiary hyperparathyroidism, anemia, cardiovascular diseases, osteitis fibrosa, adynamic bone disease, osteoporosis, steroid induced osteoporosis, senile osteoporosis, post menopausal osteoporosis, osteomalacia, bone loss post renal transplantation, gastrointestinal diseases, cancer, Alzheimer's disease, IBS, IBD, malassimilation, malnutrition, diarrhea, vascular calcification, abnormal calcium homeostasis, and hypercalcemia, the method comprising administering to a patient in need thereof an effective amount of a compound according to claim 1.

* * * * *